(12) United States Patent
Bonutti et al.

(10) Patent No.: US 9,089,323 B2
(45) Date of Patent: Jul. 28, 2015

(54) DEVICE AND METHOD FOR SECURING BODY TISSUE

(75) Inventors: Peter M. Bonutti, Effingham, IL (US); Matthew J. Cremens, Effingham, IL (US); Lawrence Crainich, Charlestown, NH (US)

(73) Assignee: P Tech, LLC, Effingham, IL (US)

( * ) Notice: Subject to any disclaimer, the term of this patent is extended or adjusted under 35 U.S.C. 154(b) by 823 days.

(21) Appl. No.: 11/358,399

(22) Filed: Feb. 21, 2006

(65) Prior Publication Data
US 2006/0200199 A1 Sep. 7, 2006

Related U.S. Application Data

(60) Provisional application No. 60/655,141, filed on Feb. 22, 2005.

(51) Int. Cl.
*A61B 17/04* (2006.01)
(52) U.S. Cl.
CPC ..... *A61B 17/0487* (2013.01); *A61B 2017/0456* (2013.01); *A61B 2017/0488* (2013.01)
(58) Field of Classification Search
CPC .............. A61B 17/0487; A61B 2017/446; A61B 2017/448; A61B 2017/488; A61B 2017/458; A61B 2017/459; A61B 2017/0401; A61B 2017/0408; A61B 2017/0409; A61B 2017/0414; A61B 2017/045; A61B 2017/0462
USPC ..... 606/148, 232; 24/132 WL, 115 A, 115 H, 24/115 N, 134 R
See application file for complete search history.

(56) References Cited

U.S. PATENT DOCUMENTS

| | | |
|---|---|---|
| 319,296 A | 6/1885 | Molesworth |
| 668,878 A | 2/1901 | Jensen |
| 668,879 A | 2/1901 | Miller |
| 702,789 A | 6/1902 | Gibson |
| 862,712 A | 8/1907 | Collins |
| 2,121,193 A | 12/1932 | Hanicke |

(Continued)

FOREIGN PATENT DOCUMENTS

| | | |
|---|---|---|
| CA | 2641580 | 8/2007 |
| CA | 2680827 | 9/2008 |

(Continued)

OTHER PUBLICATIONS

Arthrex, Protect your graft, Am J Sports Med, vol. 22, No. 4, Jul.-Aug. 1994.

(Continued)

*Primary Examiner* — Darwin Erezo
*Assistant Examiner* — Alexander Orkin

(57) ABSTRACT

The present invention provides a surgical system for securing a suture against relative movement with respect to a body tissue. The surgical system includes a fastener and medical device for positioning and securing a fastener onto a suture. The fastener includes inner and outer members that can slide together and rotate. The suture extends through the inner and outer members so that rotation of the inner member causes it to wrap the suture around it. As the suture is wound around the inner member, the fastener is drawn toward a position against the body tissue. Further rotation of the inner member allows tension to be applied to the suture. The fastener may be bonded to the suture in order to further secure the suture against relative movement with respect to the body tissue.

12 Claims, 27 Drawing Sheets

(56) References Cited

U.S. PATENT DOCUMENTS

| | | |
|---|---|---|
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss et al. |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston et al. |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kalnberz et al. |
| 4,156,574 A | 5/1979 | Boden |
| 4,164,794 A | 8/1979 | Spector et al. |
| 4,171,544 A | 10/1979 | Hench et al. |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. et al. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | Van der Zat et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,691,741 A | 9/1987 | Affa et al. |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,749,585 A | 6/1988 | Greco et al. |
| 4,750,492 A | 6/1988 | Jacobs |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |
| 4,792,336 A | 12/1988 | Hiavacek et al. |
| 4,817,591 A | 4/1989 | Klause |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A | 5/1990 | Sapega et al. |
| 4,924,866 A | 5/1990 | Yoon |
| 4,932,960 A | 6/1990 | Green et al. |

(56) References Cited

U.S. PATENT DOCUMENTS

| | | | |
|---|---|---|---|
| 4,935,026 A | 6/1990 | McFadden | |
| 4,935,028 A | 6/1990 | Drews | |
| 4,945,625 A | 8/1990 | Winston | |
| 4,946,468 A | 8/1990 | Li | |
| 4,954,126 A | 9/1990 | Wallsten | |
| 4,955,910 A | 9/1990 | Bolesky | |
| 4,957,498 A | 9/1990 | Caspari et al. | |
| 4,961,741 A | 10/1990 | Hayhurst | |
| 4,963,151 A | 10/1990 | Ducheyne et al. | |
| 4,966,583 A | 10/1990 | Debbas | |
| 4,968,315 A | 11/1990 | Gatturna | |
| 4,969,888 A | 11/1990 | Scholten et al. | |
| 4,969,892 A * | 11/1990 | Burton et al. | 606/218 |
| 4,990,161 A | 2/1991 | Kampner | |
| 4,994,071 A | 2/1991 | MacGregor | |
| 4,997,445 A | 3/1991 | Hodorek | |
| 4,998,539 A | 3/1991 | Delsanti | |
| 5,002,550 A | 3/1991 | Li | |
| 5,002,563 A | 3/1991 | Pyka et al. | |
| 5,009,652 A | 4/1991 | Morgan et al. | |
| 5,009,663 A | 4/1991 | Broome | |
| 5,009,664 A | 4/1991 | Sievers | |
| 5,013,316 A | 5/1991 | Goble et al. | |
| 5,019,090 A | 5/1991 | Pinchuk | |
| 5,021,059 A | 6/1991 | Kensey et al. | |
| 5,035,713 A | 7/1991 | Friis | |
| 5,037,404 A | 8/1991 | Gold et al. | |
| 5,037,422 A | 8/1991 | Hayhurst et al. | |
| 5,041,093 A | 8/1991 | Chu | |
| 5,041,114 A | 8/1991 | Chapman et al. | |
| 5,041,129 A | 8/1991 | Hayhurst et al. | |
| 5,046,513 A | 9/1991 | Gatturna et al. | |
| 5,047,055 A | 9/1991 | Bao et al. | |
| 5,051,049 A | 9/1991 | Wills | |
| 5,053,046 A | 10/1991 | Janese | |
| 5,053,047 A | 10/1991 | Yoon | |
| 5,059,193 A | 10/1991 | Kuslich | |
| 5,059,206 A | 10/1991 | Winters | |
| 5,061,274 A | 10/1991 | Kensey | |
| 5,061,286 A | 10/1991 | Lyle | |
| 5,069,674 A | 12/1991 | Fearnot et al. | |
| 5,078,731 A | 1/1992 | Hayhurst | |
| 5,078,744 A | 1/1992 | Chvapil | |
| 5,078,745 A | 1/1992 | Rhenter et al. | |
| 5,084,050 A | 1/1992 | Draenert | |
| 5,084,051 A | 1/1992 | Tormala et al. | |
| 5,085,660 A | 2/1992 | Lin | |
| 5,085,661 A | 2/1992 | Moss | |
| 5,098,433 A | 3/1992 | Freedland | |
| 5,098,434 A | 3/1992 | Serbousek | |
| 5,098,436 A | 3/1992 | Ferrante et al. | |
| 5,100,405 A | 3/1992 | McLaren | |
| 5,100,417 A | 3/1992 | Cerier et al. | |
| 5,102,417 A | 4/1992 | Palmaz | |
| 5,102,421 A | 4/1992 | Anspach, Jr. | |
| 5,108,399 A | 4/1992 | Eitenmuller et al. | |
| 5,120,175 A | 6/1992 | Arbegast et al. | |
| 5,123,520 A | 6/1992 | Schmid et al. | |
| 5,123,914 A | 6/1992 | Cope | |
| 5,123,941 A | 6/1992 | Lauren et al. | |
| 5,127,412 A * | 7/1992 | Cosmetto et al. | 128/898 |
| 5,133,732 A | 7/1992 | Wiktor | |
| RE34,021 E | 8/1992 | Mueller | |
| 5,141,520 A | 8/1992 | Goble et al. | |
| 5,147,362 A | 9/1992 | Goble | |
| 5,154,720 A | 10/1992 | Trott et al. | |
| 5,156,613 A | 10/1992 | Sawyer | |
| 5,156,616 A | 10/1992 | Meadows et al. | |
| 5,158,566 A | 10/1992 | Pianetti | |
| 5,158,934 A | 10/1992 | Ammann et al. | |
| 5,163,960 A | 11/1992 | Bonutti | |
| 5,171,251 A | 12/1992 | Bregen et al. | |
| 5,176,682 A | 1/1993 | Chow | |
| 5,179,964 A | 1/1993 | Cook | |
| 5,180,388 A | 1/1993 | DiCarlo | |
| 5,183,464 A | 2/1993 | Dubrul et al. | |
| 5,192,287 A | 3/1993 | Fournier et al. | |
| 5,192,326 A | 3/1993 | Bao et al. | |
| 5,197,166 A | 3/1993 | Meier et al. | |
| 5,197,971 A | 3/1993 | Bonutti | |
| 5,203,784 A | 4/1993 | Ross et al. | |
| 5,203,787 A | 4/1993 | Noblitt | |
| 5,208,950 A | 5/1993 | Merritt | |
| 5,209,776 A | 5/1993 | Bass et al. | |
| 5,217,493 A | 6/1993 | Raad et al. | |
| 5,219,359 A | 6/1993 | McQuilkin et al. | |
| 5,226,899 A | 7/1993 | Lee et al. | |
| 5,234,006 A | 8/1993 | Eaton et al. | |
| 5,234,425 A | 8/1993 | Fogarty et al. | |
| 5,236,438 A | 8/1993 | Wilk | |
| 5,236,445 A | 8/1993 | Hayhurst | |
| 5,242,902 A | 9/1993 | Murphy et al. | |
| 5,254,113 A | 10/1993 | Wilk | |
| 5,258,007 A | 11/1993 | Spetzler et al. | |
| 5,258,015 A | 11/1993 | Li et al. | |
| 5,258,016 A | 11/1993 | DiPoto et al. | |
| 5,266,325 A | 11/1993 | Kuzma et al. | |
| 5,269,783 A | 12/1993 | Sander | |
| 5,269,785 A | 12/1993 | Bonutti | |
| 5,269,809 A | 12/1993 | Hayhurst et al. | |
| 5,281,235 A | 1/1994 | Haber et al. | |
| 5,282,832 A | 2/1994 | Toso et al. | |
| 5,290,281 A | 3/1994 | Tschakaloff | |
| 5,304,119 A | 4/1994 | Balaban et al. | |
| 5,306,280 A | 4/1994 | Bregen et al. | |
| 5,306,301 A | 4/1994 | Graf et al. | |
| 5,315,741 A * | 5/1994 | Dubberke | 24/712.1 |
| 5,318,588 A | 6/1994 | Horzewski et al. | |
| 5,320,611 A | 6/1994 | Bonutti | |
| 5,324,308 A | 6/1994 | Pierce | |
| 5,328,480 A | 7/1994 | Melker et al. | |
| 5,329,846 A | 7/1994 | Bonutti | |
| 5,329,924 A | 7/1994 | Bonutti | |
| 5,330,468 A | 7/1994 | Burkhart | |
| 5,330,476 A | 7/1994 | Hiot et al. | |
| 5,330,486 A | 7/1994 | Wilk | |
| 5,336,231 A | 8/1994 | Adair | |
| 5,336,240 A | 8/1994 | Metzler et al. | |
| 5,339,799 A | 8/1994 | Kami et al. | |
| 5,349,956 A | 9/1994 | Bonutti | |
| 5,352,229 A | 10/1994 | Goble et al. | |
| 5,354,298 A | 10/1994 | Lee et al. | |
| 5,354,302 A | 10/1994 | Ko | |
| 5,366,480 A | 11/1994 | Corriveau et al. | |
| 5,370,646 A | 12/1994 | Reese et al. | |
| 5,370,660 A | 12/1994 | Weinstein et al. | |
| 5,372,146 A | 12/1994 | Branch | |
| 5,374,235 A | 12/1994 | Ahrens | |
| 5,376,126 A | 12/1994 | Lin | |
| 5,382,254 A | 1/1995 | McGarry et al. | |
| 5,383,883 A | 1/1995 | Wilk et al. | |
| 5,383,905 A | 1/1995 | Golds et al. | |
| 5,391,173 A | 2/1995 | Wilk | |
| 5,395,308 A | 3/1995 | Fox et al. | |
| 5,397,311 A | 3/1995 | Walker et al. | |
| 5,400,805 A | 3/1995 | Warren | |
| 5,403,312 A | 4/1995 | Yates et al. | |
| 5,403,348 A | 4/1995 | Bonutti | |
| 5,405,359 A | 4/1995 | Pierce | |
| 5,411,523 A | 5/1995 | Goble | |
| 5,413,585 A | 5/1995 | Pagedas | |
| 5,417,691 A | 5/1995 | Hayhurst | |
| 5,417,701 A | 5/1995 | Holmes | |
| 5,417,712 A | 5/1995 | Whittaker et al. | |
| 5,423,796 A | 6/1995 | Shikhman et al. | |
| 5,431,670 A | 7/1995 | Holmes | |
| 5,439,470 A | 8/1995 | Li | |
| 5,441,538 A | 8/1995 | Bonutti | |
| 5,443,512 A | 8/1995 | Parr et al. | |
| 5,447,503 A | 9/1995 | Miller | |
| 5,449,372 A | 9/1995 | Schmaltz et al. | |
| 5,449,382 A | 9/1995 | Dayton | |
| 5,451,235 A | 9/1995 | Lock | |
| 5,453,090 A | 9/1995 | Martinez et al. | |

(56) References Cited

U.S. PATENT DOCUMENTS

| | | |
|---|---|---|
| 5,456,722 A | 10/1995 | McLeod et al. |
| 5,458,653 A | 10/1995 | Davidson |
| 5,462,561 A | 10/1995 | Voda |
| 5,464,424 A | 11/1995 | O'Donnell, Jr. |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,580,344 A | 12/1996 | Hasson |
| 5,584,835 A * | 12/1996 | Greenfield .................... 606/232 |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Smith |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A * | 7/1997 | Kogasaka et al. ............. 606/148 |
| 5,643,295 A | 7/1997 | Yoon |
| 5,643,321 A | 7/1997 | McDevitt |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakural et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige et al. |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |

(56) References Cited

U.S. PATENT DOCUMENTS

| | | |
|---|---|---|
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A * | 8/1999 | Fong ............................ 24/459 |
| 5,941,900 A | 8/1999 | Bonutti |
| 5,941,901 A | 8/1999 | Egan |
| 5,945,002 A | 8/1999 | Leukes et al. |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto et al. |
| 5,961,499 A | 10/1999 | Bonutti |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,077,277 A | 6/2000 | Mollenauer et al. |
| 6,077,292 A | 6/2000 | Bonutti |
| 6,080,161 A | 6/2000 | Eaves, III et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,525 A * | 9/2000 | Westcott ........................ 606/216 |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,236 B1 | 1/2001 | Bonutti |
| 6,171,307 B1 | 1/2001 | Orlich |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green |
| 6,200,322 B1 | 3/2001 | Branch et al. |
| 6,217,591 B1 | 4/2001 | Egan et al. |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,238,395 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti et al. |
| 6,371,957 B1 | 4/2002 | Amrein et al. |
| 6,409,742 B1 | 6/2002 | Fulton, III |
| 6,409,743 B1 | 6/2002 | Fenton, Jr. |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,461,360 B1 | 10/2002 | Adam |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel et al. |
| 6,527,774 B2 | 3/2003 | Lieberman |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann et al. |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,592,609 B1 | 7/2003 | Bonutti |
| 6,594,517 B1 | 7/2003 | Nevo |
| 6,605,090 B1 | 8/2003 | Trieu |
| 6,610,080 B2 | 8/2003 | Morgan |
| 6,618,910 B1 | 9/2003 | Pontaoe |

(56) References Cited

U.S. PATENT DOCUMENTS

| | | |
|---|---|---|
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 * | 3/2004 | Mohtasham ............... 74/505 |
| 6,709,457 B1 | 3/2004 | Otte |
| 6,719,765 B2 | 4/2004 | Bonutti |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 * | 9/2004 | Marvel ............... 24/135 N |
| 6,818,010 B2 | 11/2004 | Eichhorn et al. |
| 6,823,871 B2 | 11/2004 | Schmieding |
| 6,860,885 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 * | 8/2006 | Bonutti et al. ............ 606/232 |
| 7,104,996 B2 | 9/2006 | Bonutti |
| 7,128,763 B1 | 10/2006 | Blatt |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,329,263 B2 | 2/2008 | Bonutti |
| 7,335,205 B2 | 2/2008 | Aeshcliamann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Raterman |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 2001/0002440 A1 | 5/2001 | Bonutti |
| 2001/0009250 A1 | 7/2001 | Herman et al. |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0062153 A1 | 5/2002 | Paul et al. |
| 2002/0103495 A1 | 8/2002 | Cole |
| 2002/0123750 A1 | 9/2002 | Eisermann et al. |
| 2002/0183762 A1 | 12/2002 | Anderson et al. |
| 2002/0188301 A1 | 12/2002 | Dallara et al. |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |
| 2003/0225438 A1 | 12/2003 | Bonutti et al. |
| 2003/0229361 A1 * | 12/2003 | Jackson ............... 606/144 |
| 2004/0010287 A1 | 1/2004 | Bonutti |
| 2004/0030341 A1 | 2/2004 | Aeschlimann et al. |
| 2004/0034357 A1 | 2/2004 | Beane et al. |
| 2004/0097939 A1 | 5/2004 | Bonutti |
| 2004/0098050 A1 | 5/2004 | Foerster et al. |
| 2004/0138703 A1 | 7/2004 | Alleyne |
| 2004/0143334 A1 | 7/2004 | Ferree |
| 2004/0147958 A1 * | 7/2004 | Lam et al. ............... 606/232 |
| 2004/0167548 A1 | 8/2004 | Bonutti |
| 2004/0193187 A1 * | 9/2004 | Boehringer et al. ......... 606/144 |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0090827 A1 * | 4/2005 | Gedebou ............... 606/72 |
| 2005/0096699 A1 * | 5/2005 | Wixey et al. ............... 606/232 |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0261684 A1 | 11/2005 | Shaolian et al. |
| 2005/0267481 A1 | 12/2005 | Carl et al. |
| 2005/0267533 A1 * | 12/2005 | Gertner ............... 606/232 |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |

(56) References Cited

U.S. PATENT DOCUMENTS

| | | |
|---|---|---|
| 2006/0122704 A1 | 6/2006 | Vresilovic et al. |
| 2006/0142799 A1 | 6/2006 | Bonutti |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235470 A1 | 10/2006 | Bonutti |
| 2006/0241695 A1 | 10/2006 | Bonutti |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0118129 A1 | 5/2007 | Fraser et al. |
| 2007/0198555 A1 | 8/2007 | Friedman et al. |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0097345 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8-140982 | 4/1996 |
| JP | 8140982 | 6/1996 |
| SU | 184396 | 7/1966 |
| WO | 91/12779 | 9/1991 |
| WO | 93/23094 | 11/1993 |
| WO | WO9408642 | 4/1994 |
| WO | 95/16398 | 6/1995 |
| WO | WO 95/31941 | 11/1995 |
| WO | WO9614802 | 5/1996 |
| WO | WO9712779 | 4/1997 |
| WO | 97/49347 | 12/1997 |
| WO | WO 97/49347 | 12/1997 |
| WO | WO9811838 | 3/1998 |
| WO | WO9826720 | 6/1998 |
| WO | WO02053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | WO2010099222 | 2/2010 |

OTHER PUBLICATIONS

Barrett et al, T-Fix endoscopic meniscal repair: technique and approach to different types of tears, Apr. 1995, Arthroscopy vol. 11 No. 2 p. 245-51.

Cope, Suture Anchor for Visceral Drainage, AJR, vol. 148 p. 160-162, Jan. 1986.

Gabriel, Arthroscopic Fixation Devices, Wiley Enc. of Biomed Eng., 2006.

Innovasive, We've got you covered, Am J Sports Med, vol. 26, No. 1, Jan.-Feb. 1998.

510k—TranSet Fracture Fixation System, Feb. 24, 2004, k033717.

510k—Linvatec Biomaterials modification of Duet and impact Suture Anchor, Nov. 19, 2004, k042966.

510k, arthrex pushlock, Jun. 29, 2005, K051219.

510k, mitek micro anchor, Nov. 6, 1996, K962511.

510k, Multitak Suture System, Jan. 10, 1997, K964324.

510k, Modified Mitek 3.5mm Absorbable Suture Anchor System, Jun. 9, 1997, K970896.

510K, Summary for Arthrex Inc.'s Bio-Interference Screw, Jul. 9, 1997, K971358.

510k, Surgicraft Bone Tie, Sep. 25, 1998, K982719.

Karlsson et al, Repair of Bankart lesions with a suture anchor in recurrent dislocation of the shoulder, Scand. j. of Med & Science in Sports, 1995, 5:170-174.

Madjar et al, Minimally Invasive Pervaginam Procedures, for the Treatment of Female Stress Incontinence . . . , Artificial Organs, 22 (10) 879-885, 1998.

Nowak et al, Comparative Study of Fixation Techniques in the Open Bankart Operation Using Either a Cannulated Screw or Suture-Anchors, Acta Orthopcedica Belgica, vol. 64-2—1998.

Packer et al, Repair of Acute Scapho-Lunate Dissociation Facilitated by the "Tag" Suture Anchor, Journal of Hand Surgery (British and European Volume, 1994) 19B: 5: 563-564.

Richmond, Modificatio of the Bankart reconstruction with a suture anchor, Am J Sports Med, vol. 19, No. 4, p. 343-346, 1991.

Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb. 1998): pp. 118-122.

Tfix, Acufex just tied the knot . . . , Am. J. Sports Med., vol. 22, No. 3, May-Jun. 1994.

Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb. 2010): pp. 286-290.

Cobb et al, Late Correction of Malunited Intercondylar Humeral Fractures Intra-Articular Osteotomy and Tricortical Bone Grafting, J BoneJointSurg [Br] 1994; 76-B:622-6.

Fellinger, et al, Radial avulsion of the triangular fibrocartilage complex in acute wrist trauma: a new technique for arthroscopic repair, Jun. 1997, Arthroscopy vol. 13 No. 3 p. 370-4.

Hecker et al, Pull-out strength of suture anchors for rotator cuff and Bankart lesion repairs, Nov.-Dec. 1993, The American Journal of Sports Medicine, vol. 21 No. 6 p. 874-9.

Hernigou et al, Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.

Ibarra et al, Glenoid Replacement in Total Shoulder Arthroplasty, The Orthopedic Clinics of NorthAmerica: Total Shoulder Arthroplasty, vol. 29 No. 3, Jul. 1998 p. 403-413.

(56) References Cited

OTHER PUBLICATIONS

Mosca et al, Calcaneal Lengthening for Valgus Deformity of the Hindfoot: Results in Children Who Had Severe, Symptomatic flatfoot and Skewfoot, J Bone Joint Surg 1195—p. 499-512.
Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
European Search Report dated Sep. 10, 2012 for EP08732724.3.
Copending U.S. Appl. No. 11/932,907—RCE Response Sep. 15, 2011.
Copending U.S. Appl. No. 11/258,795 Non-Final Office Action mailed Apr. 26, 2011.
Copending U.S. Appl. No. 11/689,670, RCE Response Sep. 19, 2011.
Copending U.S. Appl. No. 10/614,352, Final Office Action Jul. 12, 2010.
Copending U.S. Appl. No. 11/932,602 Final Response to Office Action Jun. 10, 2011.
Copending U.S. Appl. No. 11/671,556 Response filed Aug. 23, 2010.
Co-pending U.S. Appl. No. 11/438,537, Supplemental Final Rejection mailed Sep. 25, 2009.
Petition for Inter Partes Review of U.S. Patent No. 5,980,559, Filing Date Sep. 24, 2013.
Declaration of David Kaplan, PH.D. Regarding U.S. Patent No. 5,980,559, Sep. 24, 2013.
Petition for Inter Partes Review of U.S. Patent No. 7,087,073, Filing Date Sep. 24, 2013.
Declaration of Wayne J. Sebastianelli, MD Regarding U.S. Patent No. 7,087,073, Sep. 24, 2013.
Petition for Inter Partes Review of U.S. Patent No. 6,500,195, Filing Date Oct. 2, 2013.
Declaration of Dr. Philip Hardy in Support of Petition for Inter Partes Review of U.S. Patent No. 6,500,195.
Petition for Inter Partes Review of U.S. Patent No. 5,527,343, Filing Date Sep. 26, 2013, Sep. 25, 2013.
Declaration of Dr. Philip Hardy in Support of Petition for Inter Partes Review of U.S. Patent No. 5,527,343, Sep. 25, 2013.
Corrected Petition for Inter Partes Review of US Patent No. 5,921,986, Filing Date Sep. 27, 2013.
Expert Declaration of Steve E. Jordan, MD, for Inter Partes Review of US Patent No. 5,921,986, Sep. 24, 2013.
Corrected Petition for Inter Partes Review of US Patent No. 8,147,514, Filing Date Sep. 27, 2013.
Declaration of Steve Jordan for USP 8,147,514, dated Sep. 23, 2013.
Flory, Principles of Polymer Chemistry, 1953, selected pages.
Grizzi, Hydrolytic degradation of devices based on poly(DL-lactic acid) size-dependence, Biomaterials, 1995, vol. 16, No. 4, p. 305-11.
Gopferich, Mechanisms of polymer degradation and erosion, Biomaterials, 1996, vol. 17, No. 2, p. 103-114.
Gao et el, Swelling of Hydroxypropyl Methylcellulose Matrix Tablets . . . , J. of Pharmaceutical Sciences, vol. 85, No. 7, Jul. 1996, p. 732-740.
Linvatec, Impact Suture Anchor brochure, 2004.
Seitz et al, Repair of the Tibiofibular Syndesmosis with a Flexible Implant, J. of Orthopaedic Trauma, vol. 5, No. 1, p. 78-82, 1991.
Translation of FR2696338 with translator's certificate dated Sep. 17, 2013.
Translation of DE9002844.9 with translator's certificate dated Sep. 26, 2013.
Declaration of Steve Jordan for USP 5921986, dated Sep. 24, 2013.
Declaration of Dr. Steve E. Jordan for USP 8,147,514, dated Sep. 23, 2013.

\* cited by examiner

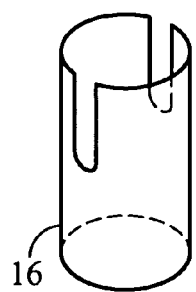 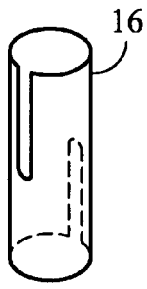 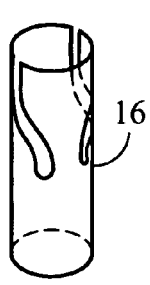 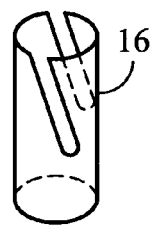
FIG. 5A        FIG. 5B        FIG. 5C        FIG. 5D
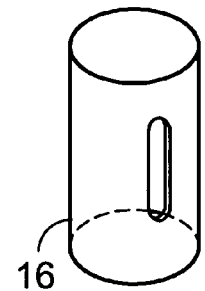 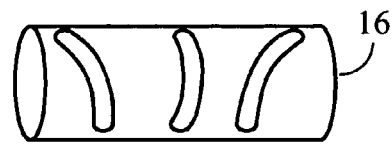 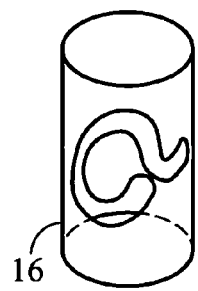
FIG. 5E        FIG. 5F        FIG. 5G

DEVICE AND METHOD FOR SECURING BODY TISSUE

CROSS-REFERENCE TO RELATED APPLICATION

This application claims the benefit of U.S. Provisional Patent Application No. 60/655,141, filed Feb. 22, 2005, entitled DEVICE AND METHOD FOR SECURING BODY TISSUE, the content of which is incorporated by reference in its entirety.

FIELD OF THE INVENTION

The invention relates to an apparatus and method for the fixation and stabilization of body tissue. More specifically, the invention relates to a fastener and medical device for the fixation and stabilization of a suture with respect to a body tissue.

BACKGROUND OF THE INVENTION

In the surgical repair of soft tissue such as the surgical reattachment of ligaments to bone or the attachment of tendon to muscle, it is known to use devices that surgically fasten the soft tissues to be repaired to the bone so as to avoid the use of suture knots. Suture knots are disadvantageous because the knot weakens a portion of the suture and reduces the overall force transmitting capability of the suture. Additionally, suture knots can also exhibit the phenomenon of "creep," where the suture can slip though the knot, resulting in a loss of tension in the suture. Suture creep can cause a change in orientation or misalignment of the attached tissue resulting in an improper healing of the attached tissue and/or pressure on or trauma to surrounding tissue.

Additionally, as a number of procedures are performed with limited surgical access, it can be difficult to form an appropriate suture knot. Furthermore, such a knot may not be uniformly tensioned and thus may slip or bind and cause pressure on or trauma to surrounding tissue.

In contrast, a fastener can be used to maintain a suture in a desired position relative to body tissue as long as the suture can be appropriately tensioned prior to its fixation and held in this tensioned state. For example, the fastener may be affixed to the suture in a manner that maintains the suture under tension. For instance, the fastener may be heated until its material reaches its transition temperature range and then plastically deformed. As the material is heated, it changes from a solid condition, in which it has a fixed form, to a soft or viscous condition. The soft or viscous material can be molded around an outer side surface of a suture and bonded to the suture without significant deformation of the suture. The transition temperature of the fastener may vary according to the material used. Some examples of various polymers which are suitable for forming fasteners are disclosed in U.S. Pat. No. 5,735,875, which is incorporated herein in its entirety. The fixation of the fastener prevents suture creep, maintaining the attached tissue in the proper orientation.

The use of fasteners helps avoid some of the deficiencies that may result from using only suture knots. One primary benefit of using fasteners is that they help properly tension the suture prior to fixation, which in turn may substantially reduce the likelihood of tensioned slip or binding of the suture that can cause excessive pressure on or trauma to the surrounding tissue. Additionally, fasteners can be used in limited access procedures.

SUMMARY OF THE INVENTION

The present invention provides a surgical system for securing a suture against movement relative to a body tissue. The surgical system includes a fastener and medical device for positioning and securing the fastener onto a suture. The surgical system can be utilized for the fixation and stabilization of body tissue, including soft tissue to soft tissue, soft tissue to bone, and bone to bone. The surgical system can additionally be used to affix implants or grafts to body tissue.

The fastener may have a first ("outer") member and a second ("inner") member, where the second member is slidably and rotatably positionable within the first member. The first member has first and second ends and an outer shell defining a longitudinal receptacle or passage along a central longitudinal axis. The second member is configured for insertion into the longitudinal passage and rotation about the central longitudinal axis. The second member includes first and second ends and a center portion interposed between the first and second ends. The first and second ends have cross sectional areas that are greater than the cross sectional area of the central portion. For instance, the second member may resemble a spool or an hourglass where the central region is smaller than the ends. The first and second members of the fastener may be bonded together in a manner that secures the suture against relative movement with respect to the body tissue. In one embodiment, for example, bonding the first and second members together involves plastically deforming at least one of the members.

The first member of the fastener may be an outer shell defining a longitudinal passage along a central longitudinal axis in which all or part of the second member may be placed or reside. The outer shell may have a pair of open ended slots at a first end and a key element positioned about a second end. The second member of the fastener may be configured for at least partial insertion into the longitudinal passage and rotatable about the central longitudinal axis. The second member may include one or more gear teeth radially positioned on or near either a first end, a second end, or both ends of the second member. A hook may be disposed on a center portion of the second member to receive or capture the suture. In addition, the first and second ends of the second member may have cross sectional areas that are larger than the cross sectional area of the center portion. It may be desirable for the first and second ends of the second member to be substantially similar in construction and/or size so that insertion of the second member into the first member does not require a particular orientation. When all or part of the second member is positioned within the first member, the key element of the first member may engage the gear teeth of the second member to prevent rotation of the second member with respect to the first member in a first direction while allowing rotation in a second, opposite direction.

In use, a suture may be positioned relative to body tissue, with at least one section of the suture extending from the body tissue. The at least one section of the suture extending from the body tissue may be captured or associated with the second member of the fastener in a manner such that axial rotation of the second member will cause the suture to wind or wrap around the second member.

The second fastener member may be moved into the longitudinal passage or receptacle of the first fastener member such that the suture extends through the first and second members of the fastener. The suture can be twisted or spiraled in the receptacle to aid in locking the suture therein. In one embodiment, the suture travels in a direction that is not parallel to the longitudinal axis of the passage or receptacle of the first member. For example, the direction of the longitudinal axis of the passage or receptacle may differ from the direction that the suture travels by about 45 to 90 degrees.

Once the fastener is assembled with the suture, the second member may be rotated with respect to the first member so that the suture starts to wind or wrap around the second member. Once the suture has reached a desired tension, energy may then be transmitted to the fastener in order to plastically deform a portion of the fastener about the suture, thereby securing the fastener to the suture.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 5A-5G depict alternative aperture and slot configurations for the shell of the fastener of FIG. 1;

DETAILED DESCRIPTION OF THE INVENTION

The present invention provides a surgical system and fastener that help secure a suture against movement relative to body tissue. The surgical system includes a medical device or instrument that helps position and secure a fastener onto a suture. The medical device systematically moves the fastener into position against the body tissue while tensioning the suture with respect to the fastener. An actuation of the medical device attaches the fastener to the suture, securing the fastener against the body tissue to prevent relative movement of the suture with respect to the body tissue.

Figure 1:
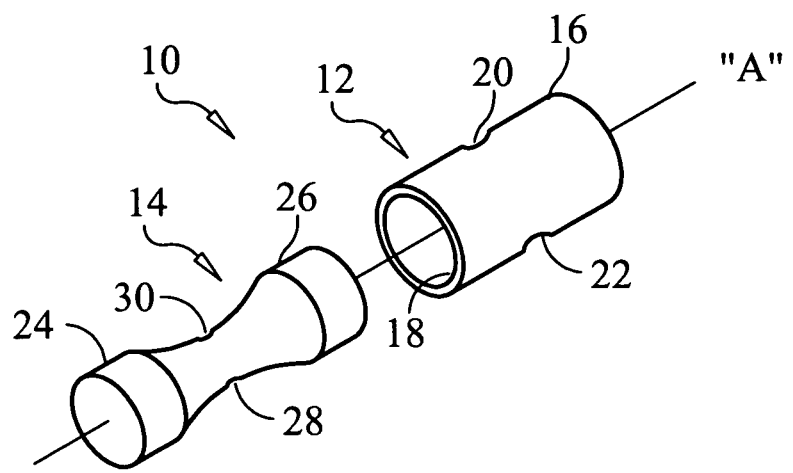
FIG. 1 depicts an exploded isometric view of a fastener of the present invention.
Figure 2:
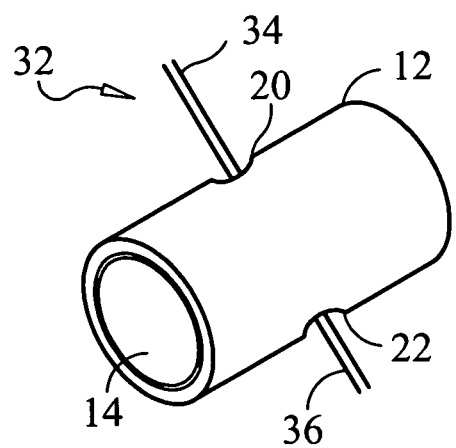
FIG. 2 depicts an isometric view of the fastener of FIG. 1.

Referring now to the drawing figures in which like reference designators refer to like elements, there is shown in FIGS. 1 and 2 a fastener 10 of the present invention including a first ("outer") member 12 and a second ("inner") member 14, wherein the second member 14 is slidably and rotatably positionable within the first member 12. The first member 12 includes an outer shell 16 defining an axial passage or receptacle 18 along a longitudinal axis "A" of the fastener 10. The axial passage may extend completely from one end of the first member to the other end, but it also may extend only partially though the first member to form a receptacle or recess where all or part of the second member may be placed. Preferably, the longitudinal axis "A" corresponds to a central longitudinal axis of the first member. One or more pairs of apertures 20 and 22 may be opposingly positioned about the circumference of the outer shell 16 of the first member 12 and are dimensioned for receiving a suture therethrough.

The second member 14 includes first and second end portions 24 and 26 disposed on opposite sides of a center portion 28. The cross sectional areas of the first and second end portions 24 and 26 may be dimensioned such that either end of the second member 14 may be slidably and rotatably positionable inside the axial passage or receptacle 18 of the first member 12. The cross sectional area of the center portion 28 is less than the cross section areas of first and second end portions 24 and 26, thereby providing clearance space between the interior surface of the outer shell 16 and the outer surface of the center portion 28.

A suture passage 30 may be provided through the center portion 28. This suture passage may be orthogonal to the central longitudinal axis "A" of the fastener 10, or alternatively may be angled or offset as described above. Slots or cutouts as described above for the first member also may be used for the suture passage 30 of the second member. Skilled artisans would appreciate, however, that consideration should be given to providing sufficient torsional strength or rigidity to the second member since its center portion 28 where the suture passage is located has a smaller cross section.

Figure 3:
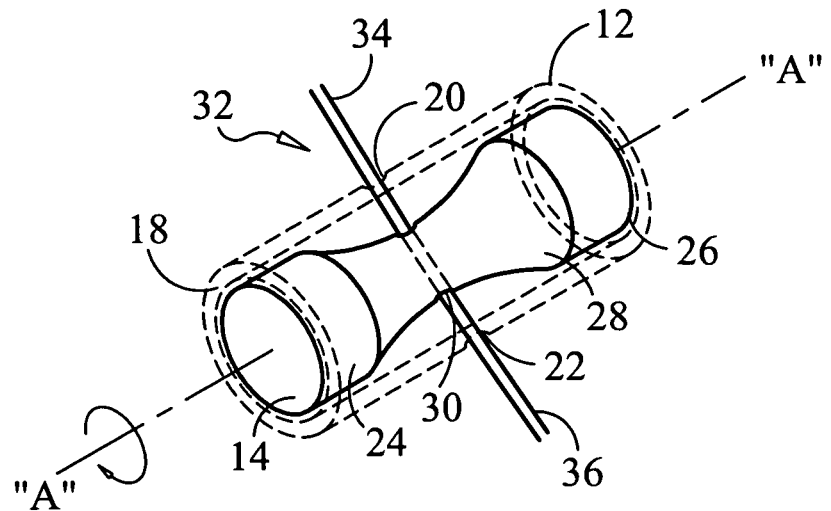
FIG. 3 depicts a sectional view of the fastener of FIG. 1, including a suture therethrough.
Figure 4:
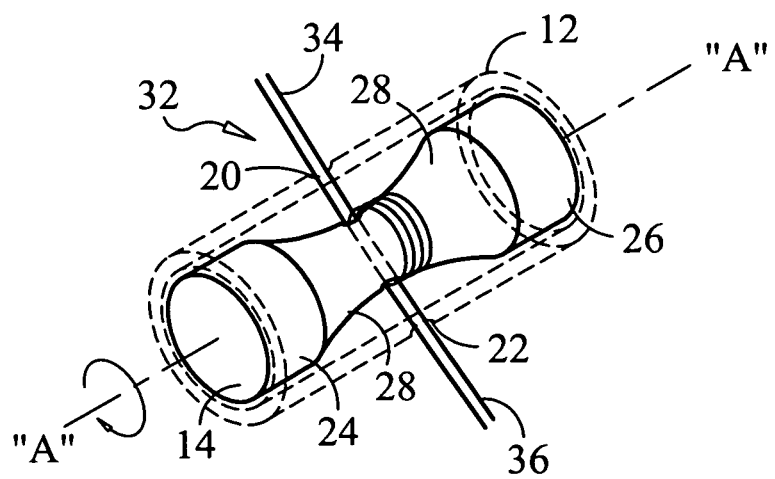
FIG. 4 depicts a sectional view of the fastener of FIG. 1, including a wrapped suture thereon.

Referring to FIGS. 3 and 4, when the second member 14 is positioned at least partially inside first member 12, the second member 14 may be rotated about longitudinal axis "A" so that the suture is wound or wrapped around its center portion 28. In a method of use, the second member 14 may be positioned within the first member 12 so that apertures 20 and 22 are aligned with the suture passage 30. A suture 32 may then be threaded through the apertures 20 and 22 and suture passage 30. Once the suture is threaded, the fastener 10 may be interposed between a first suture portion 34 having a free end and a second suture portion 36 that is connected to body tissue. The free end portion 34 may be tensioned as the second member 14 is rotated about the longitudinal axis "A". In general, the first member is maintained in a position that prevents the suture from winding or wrapping around the outside of the outer shell 16. The rotation of the second member 14 wraps or winds part of the suture 32 about the center portion 28 of the second member 14, thereby drawing the fastener 10 toward the body tissue. Rotation of the second member 14 may continue until the first member 12 is positioned adjacent to the body tissue and the suture is under a desired tension. In this manner, the fastener may apply a force to the suture 32 and body tissue that helps prevent relative movement of the suture 32 with respect to the body tissue.

Figure 10:
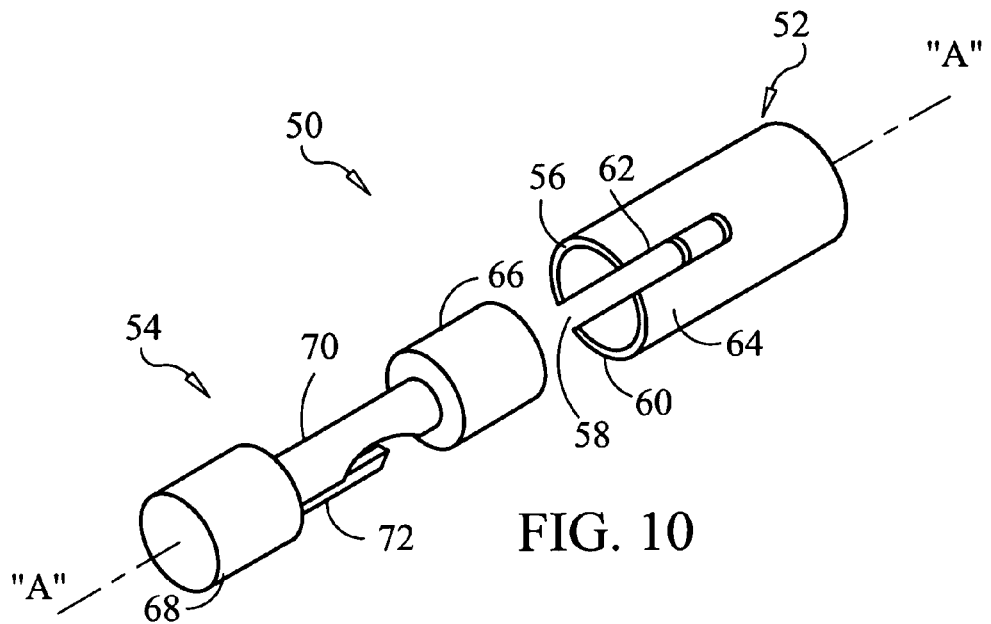
FIG. 10 depicts an exploded isometric view of an alternative fastener of the present invention.

The shell may have other configurations for receiving a suture instead of apertures. For example, as shown in FIGS. 5A-5G, the outer shell 16 may have a pair of slots that extend from a central location of the shell 16 toward one or more ends of the first member. For instance, a pair of slots may extend from a central portion of the shell 16 toward the same end of the first member, or alternatively may extend toward opposite ends. The slots may be generally linear so that they travel generally in a direction parallel to longitudinal axis A, such as illustrated in FIG. 10. Alternatively, one or more slots may curve around a portion of the shell and form a curved or arced opening.

In addition, one or more slots also may not extend fully to an end of the first member 12. Instead, they may be disposed generally in the central region of the shell 16. This enclosed slot configuration may allow for some linear adjustability of the first and second members as well as the ability for the suture to wrap over a greater area of the second member 14. In yet another embodiment, a lateral slot may extend generally in a circumferential direction around a portion of the shell so that it is generally perpendicular to longitudinal axis A. A suture may be placed inside the lateral slot and be positioned to cooperate with the second member. One potential advantage of this configuration is that the ends of the first member may be free of notches, slots or cutouts that can cause them to more easily splay or bend open when subjected to hoop stress.

Figure 6:
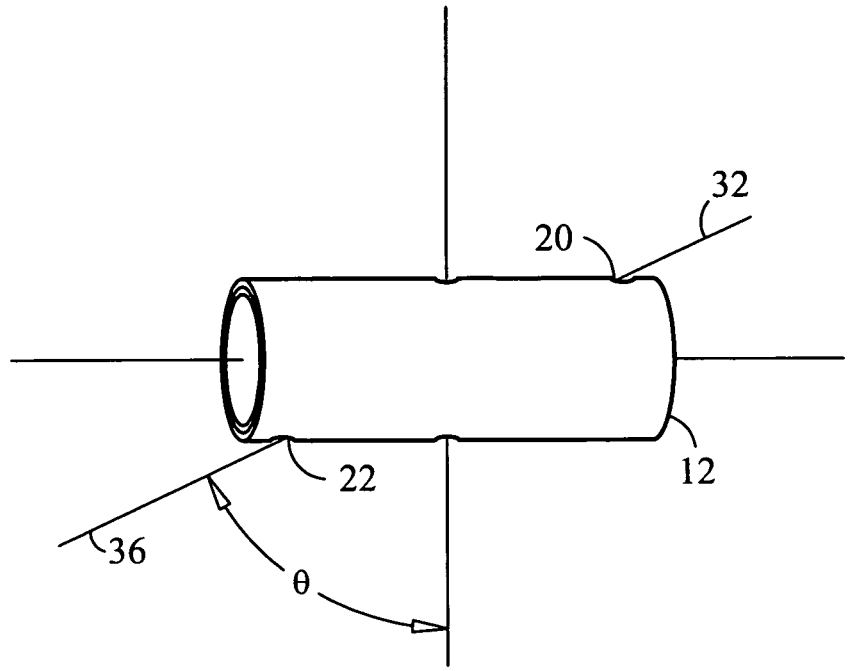
FIG. 6 depicts an angular aperture configuration for the shell of the fastener of FIG. 1.

In addition to using different types of configurations in the shell (e.g., apertures, linear slots, arced or curved slots, lateral slots, etc.) for receiving a suture, the location of the apertures or slots may be configured so that a portion of the suture disposed on one side of the shell is offset from a portion of the suture on the opposing side of the shell. For example, as shown in FIG. 6, the offset of the two openings or apertures 20, 22 may differ by an angle θ of from about 5 to 30 degrees from a perpendicular line to longitudinal axis A. Likewise, if a lateral slot is used, it too may be formed at an angle to provide a similar offset. This offset configuration may be useful in helping reduce entanglement of the suture portions as they are wound or wrapped around the second member.

After the fastener 10 has been moved into position against the body tissue, the first and second members 12 and 14 are interconnected or secured in a manner that prevents further relative movement between them. For example, a mechanical locking device, such as a pin inserted through the first and second members 12 and 14, may be applied to the fastener 10. Other mechanical locking devices, such as ratchets and the like, may also be used and are described more fully below.

Alternatively, a compressive force may be applied so that the fastener 10 plastically deforms the first and second members 12 and 14 and crimps them together. The plastic deformation may cause the first and second members 12 and 14 to bond together or simply may create an interference that can not be overcome by tension forces of the suture.

In another embodiment, energy may be applied to the fastener 10 to bond or fuse the first and second members 12 and 14 together, preventing relative movement there between. For example, the applied energy may be heat, or may be converted into heat, so that portions of the material forming the first or second members, or both, reach a transition temperature range where the material flows more easily. The material may then be plastically deformed, fused, or otherwise bonded or held together.

Different types or intensities of energy can be combined or used individually to plastically deform, partly intermix, fuse, or bond the first and second fastener members together. Some examples of types of energy that may be used include, but are not limited to, ultrasound energy, ultrasonic energy, radio frequency (RF) energy, laser energy, infrared energy, microwave energy, electromagnetic energy, resistive heat energy, contact heating energy, and exothermic chemical reactions. The energy also may be used to activate an epoxy component, compound, or constituent part of one fastener member to chemically react with an epoxy component, compound, or constituent part of the other fastener member.

Figure 7:
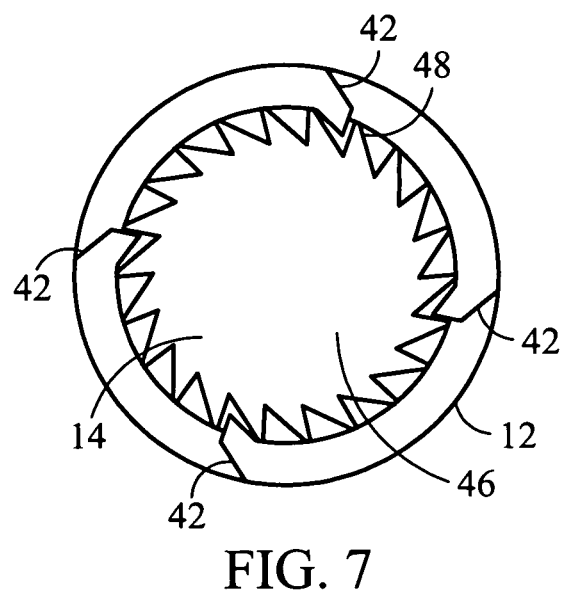
FIG. 7 depicts a ratcheting system for a fastener of the present invention.
Figure 8:
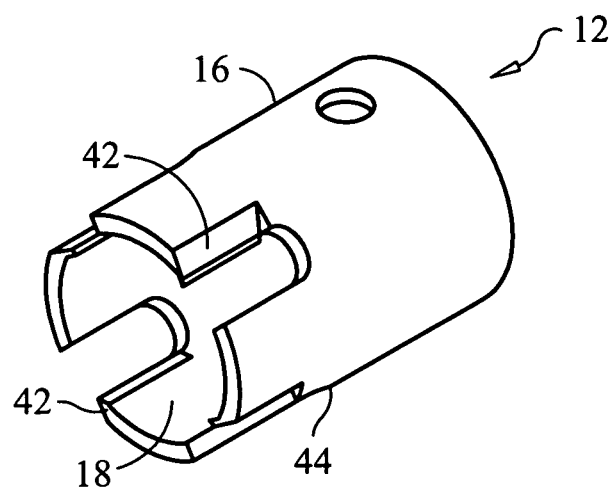
FIG. 8 depicts a key element of the ratchet system of FIG. 7.
Figure 9:
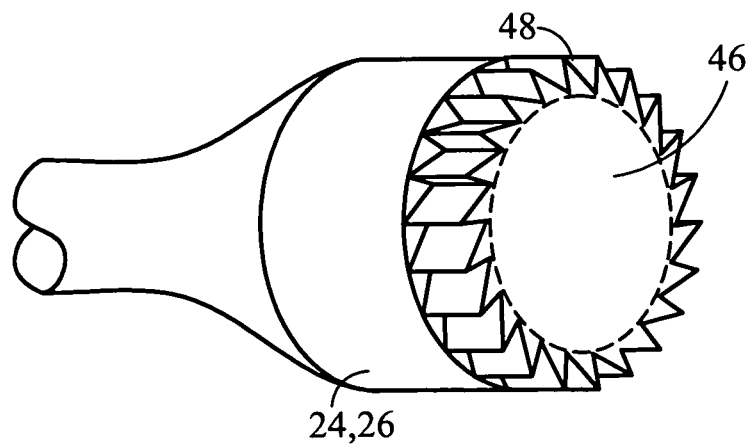
FIG. 9 depicts a gear element of the ratcheting system of FIG. 7.

In one embodiment, the fastener 10 may include a ratcheting mechanism that allows rotation in one direction, but not in an opposite direction. Thus, a ratcheting mechanism may be used to help prevent an unwinding of the suture 32 from the second member 14. Referring to FIGS. 7-9, an exemplary ratcheting system of the present invention is provided. The first member 12 of the fastener 10 includes at least one key element 42 circumferentially positioned about an end portion 44 of the outer shell 16. The key element 42 may be formed from bending a portion of the end of the shell inwards toward the center of the first member, such as illustrated in FIG. 8. Alternatively, one or more key elements 42 may be formed on the interior surface of the axial passage 18. More than one key element may be provided as well. For instance, the interior surface of the axial passage 18 may have a plurality of inwardly projecting key teeth that are angled to allow gear teeth 48 on the second member 14 to slip over them in one direction, but not in the other.

The second member 14 of the fastener 10 includes an integrated gear portion 46 having a one or more angled gear teeth 48 radially positioned about one or both end portions 24 and 26. Upon insertion of the second member 14 into the axial passage 18 of the first member 12, the key element 42 engages the gear portion 46 of the second member 14. The angular positioning of the gear teeth 48, the key element 42, or both allow the second member 14 to be rotated in only one direction.

Preferably the key elements (or their teeth), the gear teeth, or both are present in sufficient number to provide discrete control mechanism against unwinding so that small intervals of rotation, such as less than about 10 degrees, and more preferably less than about 5 degrees, will cause the key element 42 and gear teeth 48 to shift from a first interlocking position to a second interlocking position. When in an interlocking position, rotation in an opposite or unwinding direction is prevented by the engagement of the key element 42 with the gear teeth 48.

In an exemplary method of use, upon positioning of the second member 14 within the first member 12, the key element 42 engages the gear portion 46 of the second member 14. The free end portion 34 of the suture 32 is tensioned and the second member 14 is rotated in a first direction, about the central longitudinal axis "A," with respect to the first member 12. The rotation of the second member 14 wraps the connected end portion 36 of suture 32 about the center portion 28 of the second member 14, drawing the fastener 10 to the body tissue. The engagement of the key element 42 with the gear teeth 48 prevents the second member 14 from rotating in a second direction, opposite from the first direction, and unwrapping the connected end portion 36 of suture 32 from the center portion 28 of the second member 14. Rotation of the second member 14 may continue until the first member 12 is positioned adjacent to the body tissue. Further rotation of the second member causes the fastener 10 to apply a force to the suture 32 and body tissue, thereby preventing relative movement of the suture 32 with respect to the body tissue. The force tensions the suture 32 to a predetermined tension, where the tension in the suture can be measured with a sensor. Alternatively, the force applied to the tissue can be measured with a sensor, for example, a sensor can measure the change in resistance of the tissue as the force is applied to the tissue, decreasing the tissue thickness.

As previously disclosed, after the fastener 10 has been moved into position against the body tissue, the first and second members 12 and 14 may be interconnected to help prevent further relative movement between them. The ratchet configuration described above may be sufficiently capable of preventing undesired unwinding without modification. Thus, even though relative movement in winding direction may be possible, the configuration may be sufficient to prevent unwinding. Thus, in some cases prevention of relative movement in one direction (e.g., unwinding) may be sufficient.

As described above, mechanical fasteners also may be applied to the fastener 10 to prevent any relative movement or at least to prevent unwinding. Alternatively, a compressive force may be applied to the fastener 10, plastically deforming the first and second members 12 and 14. The plastic deformation may bond the first and second member 12 and 14 together or cause an interference that prevents relative movement. Once again, one alternative would be to expose the fastener 10 to an energy that bonds the first and second members 12 and 14 together.

Figure 11:
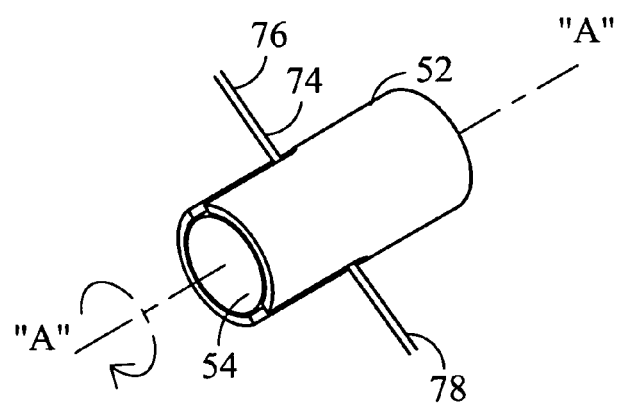
FIG. 11 depicts an isometric view of the fastener of FIG. 10.

Referring now to FIGS. 10 and 11 an alternative fastener 50 of the present invention is provided. Fastener 50 includes a first ("outer") member 52 and a second ("inner") member 54. The second member 54 is at least partly slidably and rotatably positionable within the first member 52. The first member 52 includes an outer shell 56 defining an axial passage 58 along a central longitudinal axis "A" of the fastener 50. A pair of slots 60 and 62 are positioned about the circumference of an end portion 64 of the outer shell 56 of the first member 52 and are dimensioned for receiving a suture there through.

The second member 54 includes first and second end portions 66 and 68 having a center portion 70 disposed there between. The center portion 70 includes a hook member 72 configured for capturing a suture. The cross sectional areas of the first and second end portions 66 and 68 are dimensioned such that the second member 54 is slidably and rotatably positionable through the axial passage 58 of the first member 52. The cross sectional area of the center portion 70 is less than the cross section areas of first and second end portions 66 and 68, providing spacing between the outer shell 56 of the first member 52 and the center portion 70 of the second member 54.

The second member 54 is positionable within the first member 52, wherein the second member 54 is rotatable about the central longitudinal axis "A" with respect to the first member 52. In a method of use, the second member 54 may be extended from (i.e., disposed at least partly outside of) the first member 52. The hook member 72 may be used to capture a suture 74. The second member 54 may be positioned within the first member 52, drawing the captured suture 74 into the slots 60 and 62 of the first member 52. As discussed above, any of the alternative embodiments discussed above for the first and second members shown in FIGS. 1-9 also may be utilized with this embodiment, and likewise the hook or other features of this embodiment may be used with other embodiments described herein.

Once the suture 74 is positioned through the hook member 72 and the slots 60 and 62, such that the fastener 50 is interposed between a first suture portion 76 having a free end and a second suture portion 78 that is connected to body tissue, the physician may begin the suture winding or wrapping process. The free end portion 76 of the suture 74 may be tensioned as the second member 54 is rotated about the central longitudinal axis "A". The rotation of the second member 54 wraps the connected end portion 78 of suture 74 about the center portion 70 of the second member 54, drawing the fastener 50 to the body tissue. The second member 54 may continue to be rotated until the first member 52 is positioned adjacent the body tissue. Further rotation of the second member 54 once again causes the fastener to apply a force to the suture 74 and body tissue, thereby preventing relative movement of the suture 74 with respect to the body tissue.

After the fastener 50 has been moved into position against the body tissue, the first and second members 52 and 54 are interconnected, preventing relative movement there between. As previously disclosed, a variety of techniques and devices may be used to either prevent unwinding movement between the first and second fastener members, or to prevent any relative movement between them. Some examples include mechanical locking devices, ratchets, compressive forces, crimping, plastic deformation, bonding, exposure to one or more types or intensities of energy, or the like.

Figure 12:
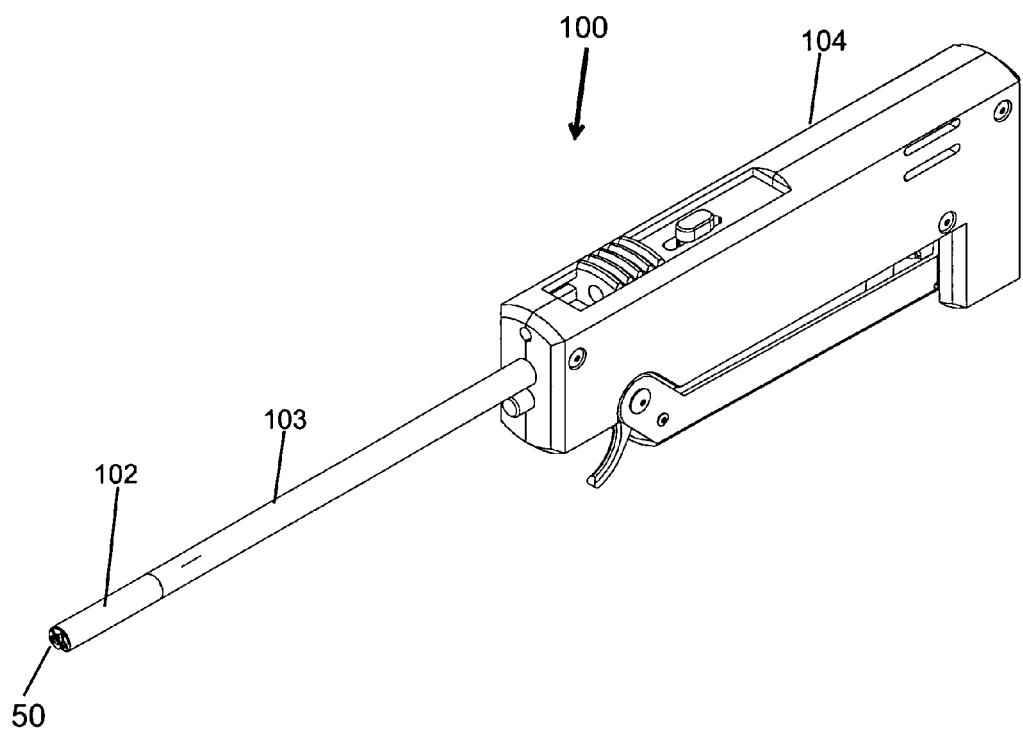
FIG. 12 depicts a medical device of the present invention.

Referring to FIG. 12, a medical device 100 for applying a fastener 50 of the present invention is provided. The medical device 100 includes a tip 102 and a handle 104, wherein a tubular member 103 is interposed between and connected to the handle 102 and the tip 104. The fastener 50 is supported in the tip 102 such that an actuation of a transfer mechanism extends the second fastener member 54 from the first fastener member 52 to capture the suture 74. Upon capture, a ratcheting mechanism draws the fastener 50 to the body tissue, applying a tension to the suture 74 and the body tissue to prevent relative movement between the suture 74 and the body tissue. A fixation mechanism secures the fastener 50 to the suture by exposing the fastener 50 to one or more energy sources, thereby bonding the first and second members 52 and 54 of the fastener 50 together. An ejector mechanism ejects the bonded fastener 50 from the medical device 100.

Figure 13:
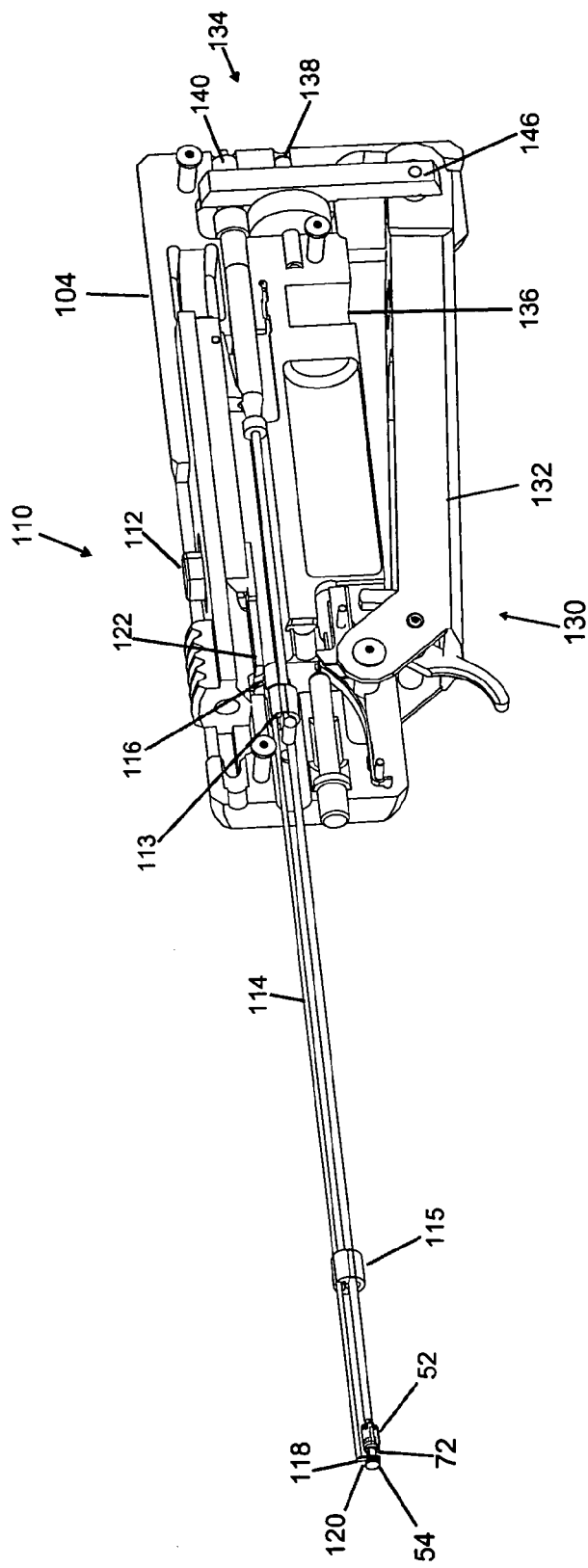
FIG. 13 depicts a sectional view of the medical device of FIG. 12.
Figure 14:
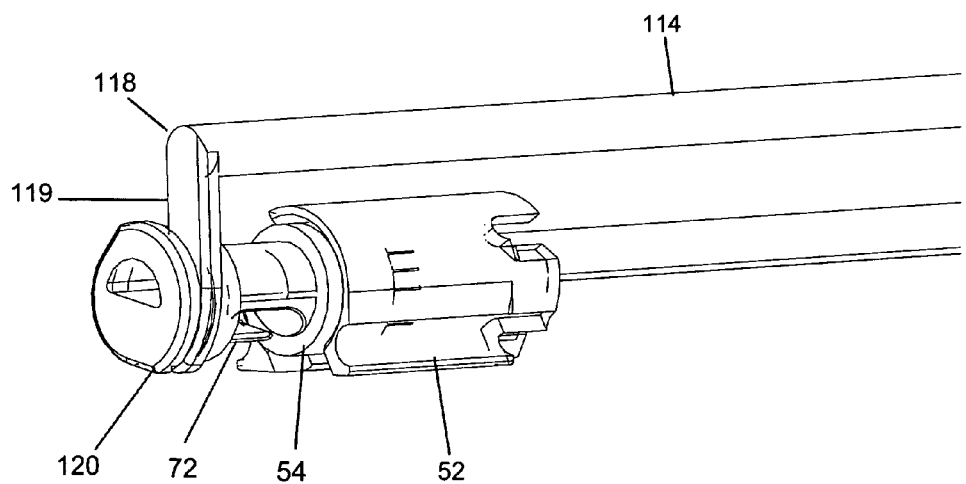
FIG. 14 depicts a sectional view of the medical device of FIG. 12 showing the tip portion of the transfer mechanism.

Referring to FIGS. 13 and 14, a transfer mechanism 110 includes a transfer actuator 112 and a transfer rod 114. The transfer actuator 112 is slidably positionable within the handle 104 of the medical device 100, such that the transfer mechanism 110 is actuatable from a closed position to an open position. When the transfer mechanism is in a closed position, the second fastener member 54 is positioned substantially within, and perhaps fully within, the first fastener member 52, which is disposed in the tip 102 of the medical device 100.

To actuate the transfer mechanism 110 from the closed position to the open position, the transfer actuator 112 may be slid within the handle 104 to engage a first end 116 of the transfer rod 114. First and second tube supports 113 and 115 support the transfer rod 114 through tubular member 103 (not shown). During actuation of the transfer mechanism, the transfer rod 114 is moved through the tip 102 such that a second end 118 of the transfer rod 114 extends outward from the tip 102 away from the handle 104.

The second end 118 of the transfer rod 114 engages an end portion 120 of the second fastener member 54. For example, the second end 118 of the transfer rod 114 includes a swing arm 119 for engaging a radial channel about end portion 120 of the second fastener member 54.

As the second end 118 of the transfer rod 114 is extended from the tip 102, the second fastener member 54 is drawn out from the first fastener member 52, extending from the tip 102. In such a configuration, the medical device 100 is able to receive the suture 74 within hook 72.

Upon capture of the suture 74 in the hook 72, the transfer mechanism 110 is actuated from the open position to the closed position. The transfer actuator 112 may be slid within the handle 104 of the medical device 100 such that the transfer actuator 112 disengages the first end 116 of the transfer rod 114. A transfer biasing member 122 engages the first end 116 of the transfer rod 114 and moves the rod into the closed position. This movement of the transfer rod 114 causes the second fastener member 54 and the captured suture 74 to be moved at least partly, and possibly fully, into the first fastener member 52.

A ratcheting mechanism may be used to draw the fastener 50 to the body tissue and secure the suture 74 against relative movement with respect to the body tissue. Referring to FIG. 13, a ratcheting mechanism 130 includes a ratchet trigger 132 operably connected to a gear mechanism 134. The ratchet trigger 132 is illustrated as being pivotally connected to the handle 104 of the medical device 100, although skilled artisans would appreciate that the ratchet also may be operatively connected to the device in other ways. A ratchet trigger return 136 is provided so that the ratchet may be used repeatedly. With respect to FIG. 13, the ratchet return 136 is interposed between the ratchet trigger 132 and the handle 104. The trigger return 136 in this embodiment is illustrated as a coiled or helical spring, in view of the disclosure herein it should be understood that the trigger return 136 of this embodiment also may be a pressurized gas in a deformable chamber, a foamed material, a cantilever spring, or the like.

Figure 15:
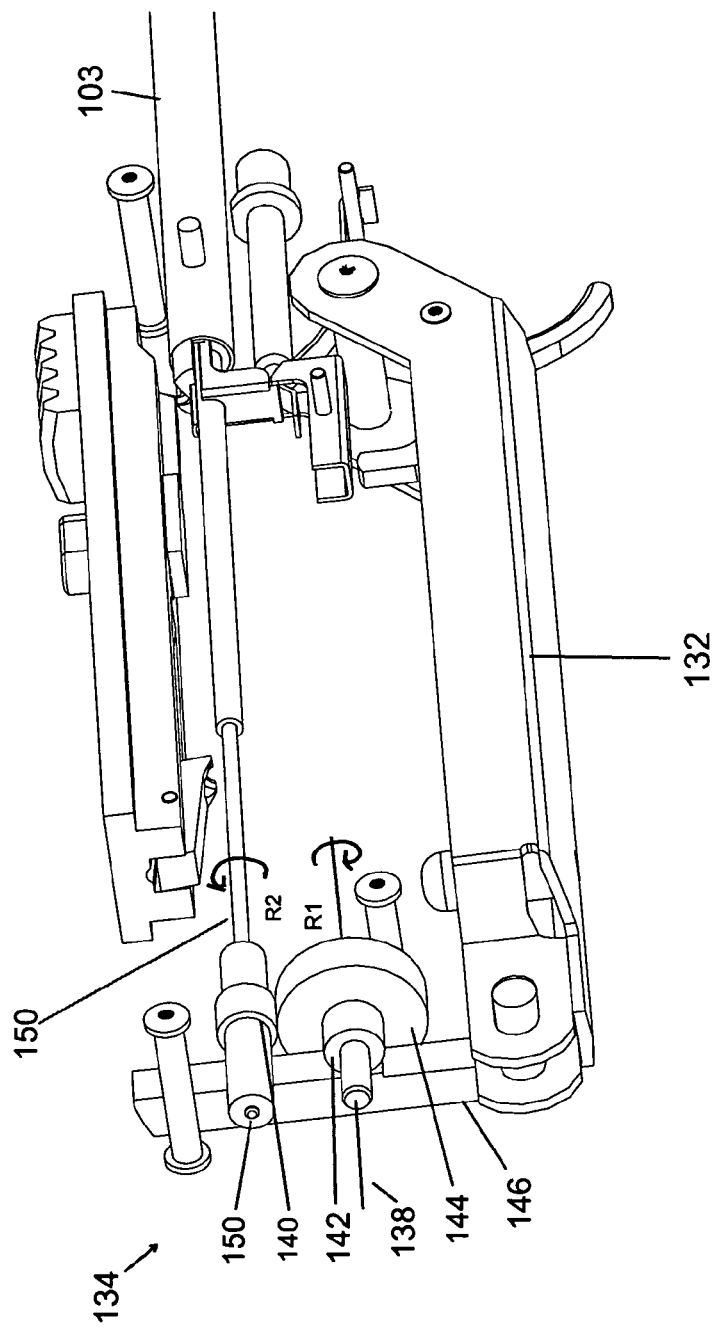
FIG. 15 depicts a sectional view of the medical device of FIG. 12 showing the handle portion of the ratcheting mechanism.

Turning to FIG. 15, the gear mechanism 134 or the ratchet 130 may have first and second gear systems 138 and 140 mounted in the handle 104 of the medical device 100. The first gear system 138 includes a first gear 142 and a second gear 144. The first gear 142 is operably connected to the ratchet trigger 132 with a ratchet member 146, such that as the ratchet trigger 132 is moved from a first position to a second position, the ratchet member 146 causes the first gear system 138 to rotate in a first direction R1. The second gear system 140 is engagingly connected to the second gear 144 of the first gear system 138, such that as the first gear system 138 is rotated in the first direction R1 the second gear system 140 is caused to rotate in a second direction R2, opposite from the first direction R1.

When the ratchet trigger 132 is released, the trigger return 136 moves the trigger from the second position to its original, first position. The operable connection between the ratchet member 146 and the first gear 142 is such that the ratchet member 146 does not cause the first gear 142 and first gear system 138 to rotate as the ratchet trigger 132 is moved from the second position to the first position. For example, the ratchet member 146 includes a plurality of angular key members which engage the teeth of the first gear 142 as the ratchet trigger 132 is moved from the first position to the second position. As the ratchet trigger 132 is moved from second position to the first position the angular key members of the ratchet member 146 disengage the teeth of the first gear 142, permitting the ratchet trigger 132 to be moved from second position to the first position without a rotating the first gear 142. A continuous, repetitive, movement of the ratchet trigger 132 from the first to the second positions results a ratcheting rotation of the second gear system 140.

The second gear system 140 is affixed to a center rod 150 of the medical device 100. As the second gear system 140 is rotated in the second direction R2 the center rod 150 is rotated in the second direction R2. The center rod 150 traverses the medical device 100, through the handle 104 and the tubular member 103 to the tip 102, and may be supported by the first and second tube supports 113 and 115.

Figure 16:
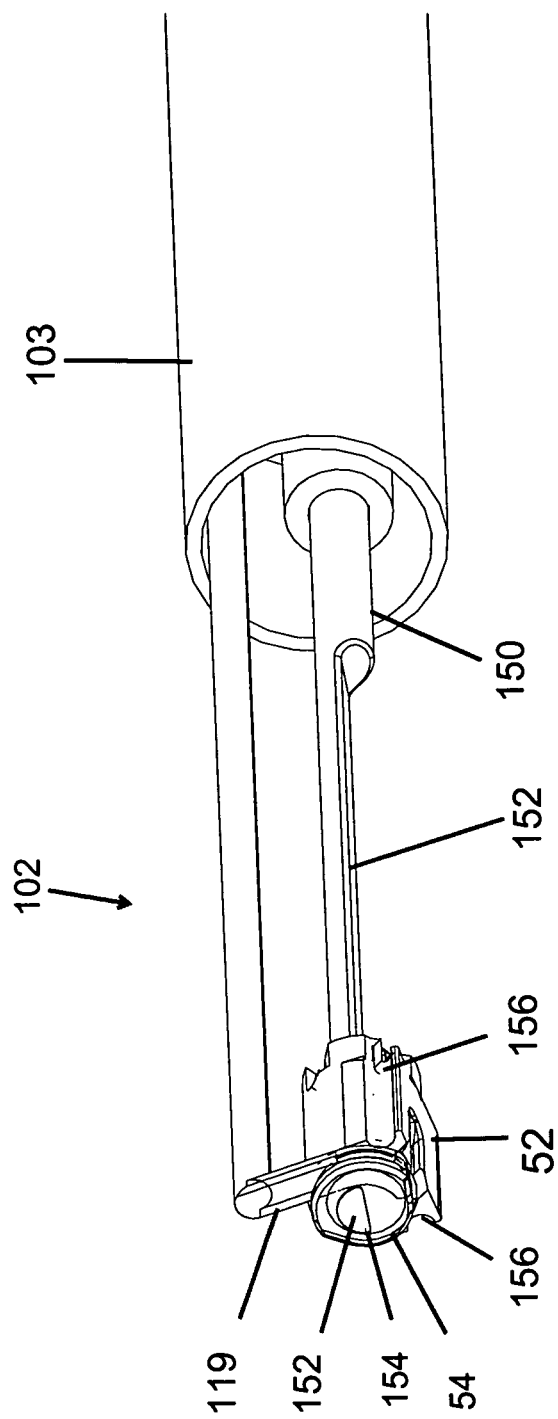
FIG. 16 depicts a sectional view of the medical device of FIG. 12 showing the tip portion of the ratcheting mechanism.

Referring to FIG. 16, the center rod 150 engages the second fastener member 54, such that as the center rod 150 is rotated the second fastener member 54 also is rotated in a suture winding direction. The end 152 of the center rod 150 is shaped to slidingly engage an instrument passage 154 through the second member 54 of the fastener 50. Thus, the center rod end 152 and second member may interact similarly to a key in a keyway or as a tool such as a screwdriver, hex wrench, or the like fitting in a matched receptacle.

For example, the center rod end portion 152 and instrument passage 154 each have a substantially hemi-cylindrical cross sectional area. As mentioned above, other matched shapes for the center rod end portion 152 and instrument passage 154 may be used, such as a multi-sided geometric shapes (e.g., a rectangular, triangular, square, pentagonal, hexagonal, star, cross, hemi circular shapes, etc.). Thus, it is contemplated that the cross-sectional area of the center rod end portion 152 and instrument passage 154 can be any shape that allows the engagement and rotation of these two components.

Figure 17:
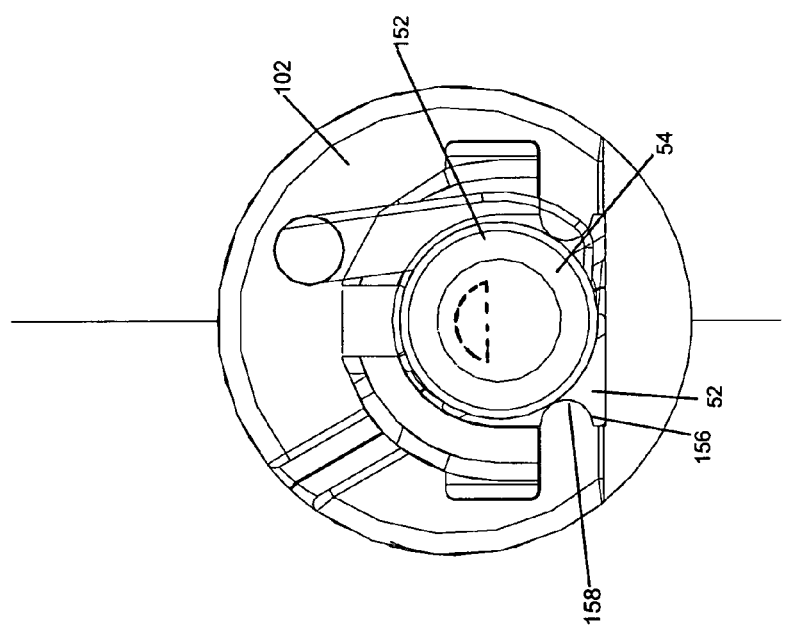
FIG. 17 depicts a front view of the medical device of FIG. 12 showing the tip portion of the ratcheting mechanism.

The first fastener member 52 may be positioned within the tip 102 of the medical device 100 such that the second fastener member 54 is rotatable with respect to it. In the embodiment shown in FIG. 16, the first fastener member 52 includes a pair of longitudinal channels 156 that are slidingly engagable with the tip 102. Referring to FIG. 17, the tip 102 includes a pair of longitudinal extensions 158. The first fastener member 52 may be positioned in the tip 102 such that the longitudinal extensions 158 engage the longitudinal channels 156 and prevents rotation of the first member 52 as the second member 54 is rotated.

In use, ratchet trigger 132 is repeatedly moved from the first to the second to the first position, ratcheting (rotating) the center rod 150 in the second direction R2. The rotation of the center rod 150 rotates the second fastener member 54 in a winding direction with respect to the first fastener member 50. As the second fastener member 54 is rotated, the captured suture 74 is wound about the center portion 70 of the second member 54. The second member 54 may continue to be rotated, thereby drawing the tip 102 of the medical device 100 and the first fastener member 52 to the body tissue. Further rotation causes tension to be applied to the suture 74 and forces to be applied to the body tissue. Once a desired force is reached, rotation may be stopped and the suture 74 is restrained from movement relative to the body tissue.

Figure 18:
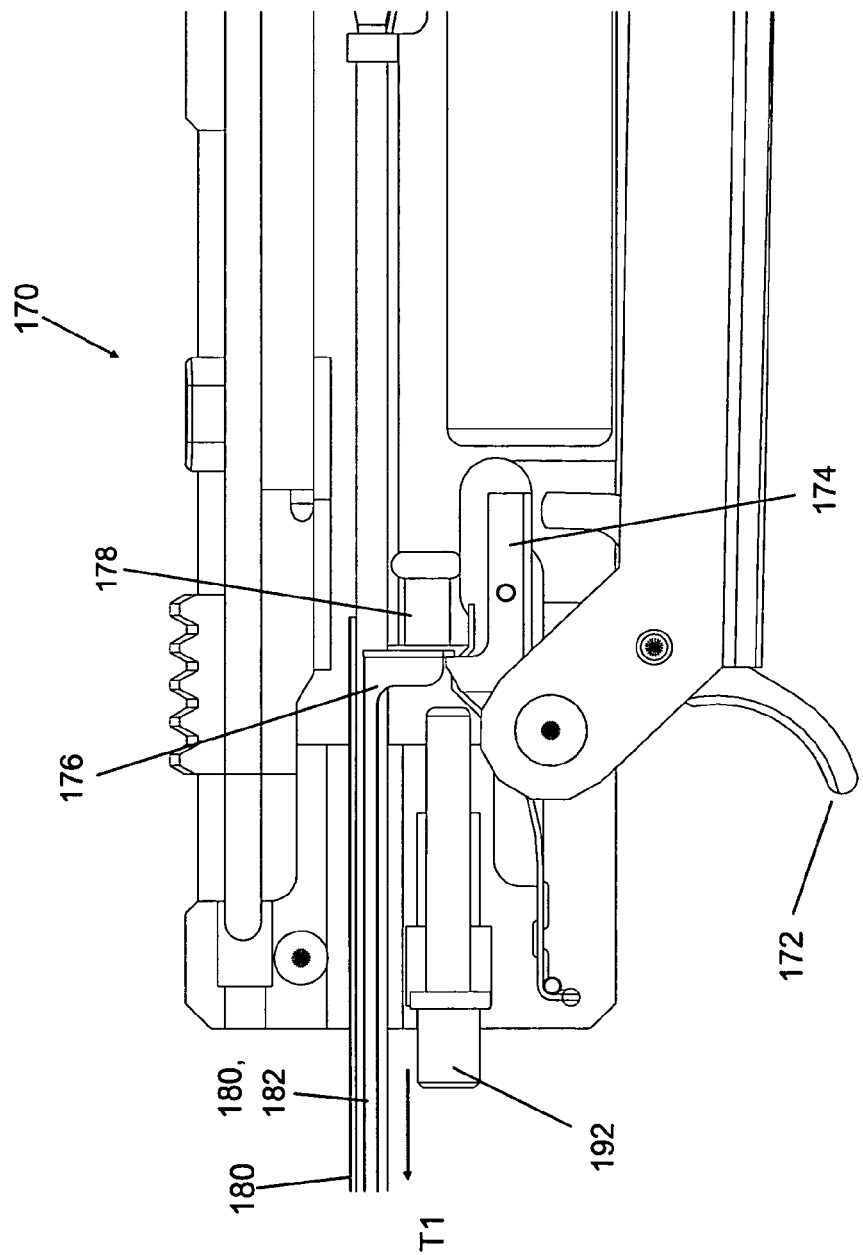
FIG. 18 depicts a sectional view of the medical device of FIG. 12 showing the handle portion of the fixation mechanism.

The fixation mechanism may be used to bond the first and second fastener members 52 and 54 together, thereby securing the fastener 50 to the suture 74 and preventing relative movement between the suture 74 and the body tissue. Referring to FIG. 18, a fixation mechanism 170 includes a force application system and an energy system. The force application system includes a cam lock 174 biased to support a dual cam member 176 in a first position. The actuation of the second trigger 172 pivots the cam lock 174 to disengage the dual cam member 176. A cam biasing member 178 translates the dual cam member 176 from the first position in the first direction T1.

Figure 19:
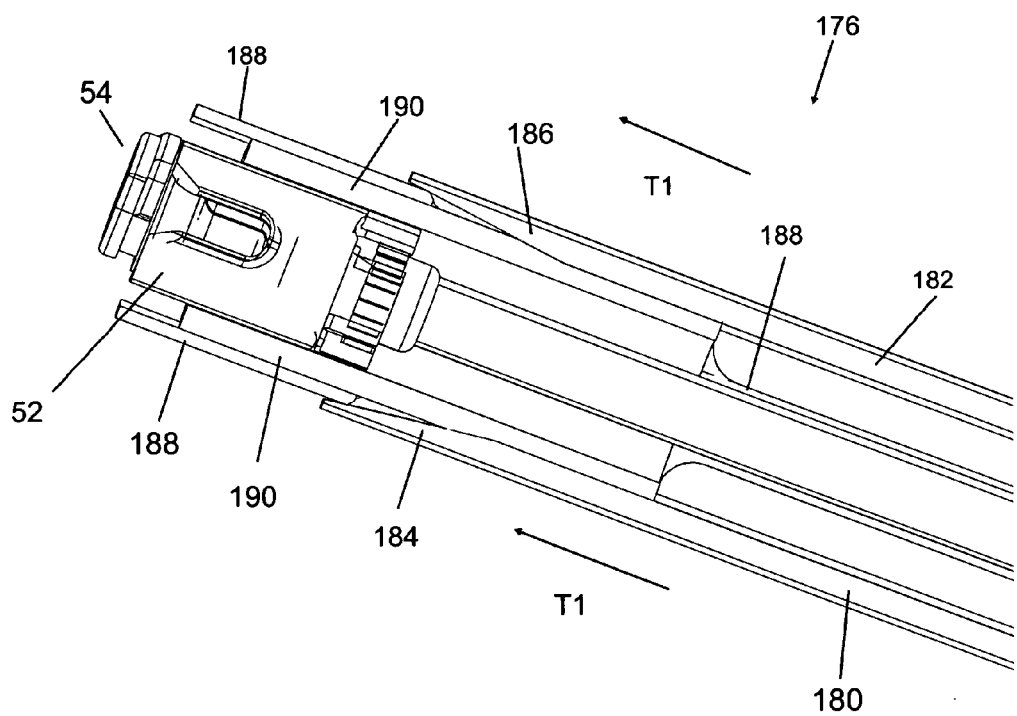
FIG. 19 depicts a sectional view of the medical device of FIG. 12 showing the tip portion of the fixation mechanism.

Referring to FIG. 19, the dual cam member 176 includes first and second cam members 180 and 182, each having angular tips 184 and 186. The angular tips 184 and 186 are positioned proximal to an energy element 188, which at least partially surrounds the fastener 50. An energy shroud 190 is interposed between the energy element 188 and fastener 50.

As noted above, an actuation of the second trigger 172 disengages the cam lock 174, allowing the cam biasing member 178 to translate the dual cam member 176 in a first direction T1. The translation of the dual cam member 176 translates the angular tips 184 and 186 of the first and second cam members 180 and 182 onto the energy element 188. The angular configuration of the tips 184 and 186 imparts a compressive force to the energy element 188 as the first and second cam members 180 and 182 are biased in the first direction T1, compressing the energy element 188 and the energy shroud 190 about the fastener 50.

Additionally, the translation of the dual cam member 176 activates the energy system to apply energy to the fastener 50, bonding the first and second fastener members 52 and 54. The translation of the dual cam member 176 in the first direction T1 activates a first switch SW1. The first switch SW1 closes a circuit, connecting the energy element 188 to an energy source. The energy element 188 provides energy, through energy shroud 190, to the fastener 50 to bond the first and second members 52 and 54 together. At least a portion of the applied energy is converted into heat, which causes the temperature of the fastener material to be elevated to a softening or transition temperature range. When in this range, one or all parts of the fastener may be subjected to plastic deformation.

The dual cam member 176 continues to translate in the first direction T1 as the first and/or second fastener members 52 and 54 are plastically deformed by the angular tips 184 and 186. The tips may be configured to impart an increasing compressive force onto the fastener 50. The combined application of the compressive force and energy to the fastener 50 results in the bonding or interlocking of the first and second member 52 and 54. The energy element 188 is disconnected from the energy source upon achieving a desired plastic deformation of the fastener 50.

The amount of plastic deformation may be preselected in some embodiments. For example, at the pre-selected plastic deformation of the fastener 50, the dual cam member 176 will have translated to a second position and engage with a second switch SW2. The engagement of the dual cam member 176 with the second switch SW2 opens the circuit and disconnects the energy source from the energy element 188. The fastener may then cool until its temperature falls below a transition state where the material is less likely or not expected to flow.

The fixation mechanism 170 is reset by actuating the reset button 192. The reset button 192 engages the dual cam member 174, translating the dual cam member 176 from the second position to the first position. The translation of the dual cam member 176 from the second position to the first position closes the second switch "SW2" and opens the first switch "SW1." The biased cam lock 174 reengaged the dual cam member 176, supporting the dual cam member 176 in the first position. The fixation mechanism 170 can be reset, optionally, upon the completion of the bonding of the fastener or after the ejection of the fastener 50 from the tip portion 102 of the medical device 100.

Figure 20:
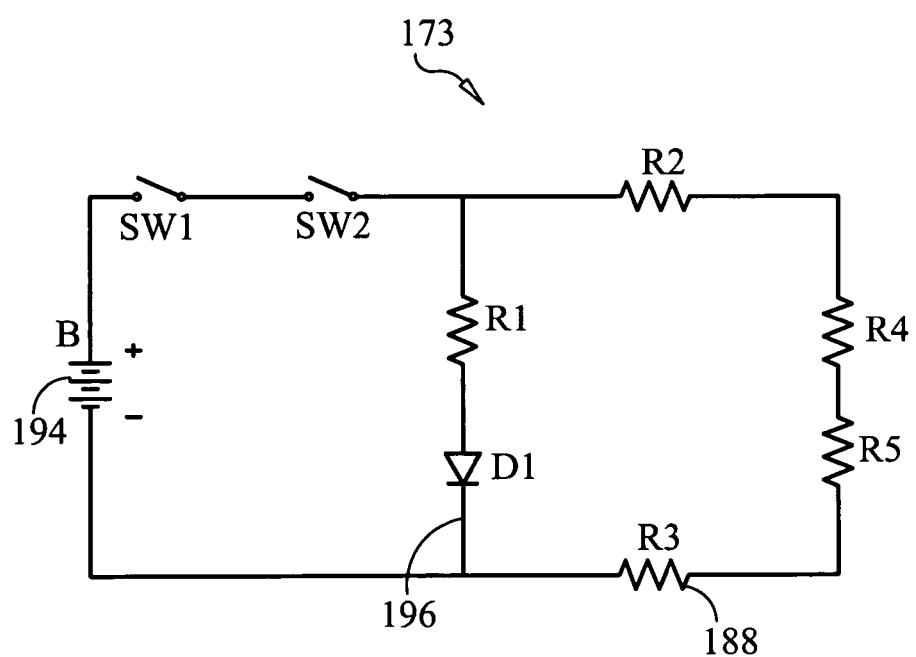
FIG. 20 depicts a schematic diagram of an energy system of the present invention.

Referring to FIG. 20, an exemplary energy system 173 of the presented invention is provided. The energy element 188 includes serially connected resistors R2 and R3 and heating elements R4 and R5. The resistors and heating elements are connected to the energy source 194, wherein switched SW1 and SW2 are inline with the energy source 194 and the resistors and heating elements. The switch SW1 is initially positioned in an open position and the switch SW2 is initially positioned in a closed position. As disclosed above, the translation of the dual cam member 176 in the first direction T1 activates switch SW1, closing the circuit and connecting the energy source 194 to the heating elements. The heating elements R4 and R5 generate heat, applying heat energy to the fastener 50, plastically deforming the first and second members 52 and 54.

At the pre-selected plastic deformation of the fastener 50, the dual cam member 176 will have translated to a second position, engaging switch SW2. The engagement of the dual cam member 176 with switch SW2 opens the circuit, disconnecting the energy source 194 from the resistors R2, R3, R4, and R5.

The electric system 173 can further include an activation indicator, providing a visual or audible indication the application of energy to the fastener 50. For example, the activation indicator 196 includes LED D1 and current limiting resistor R1. An activation of switch SW1 provides energy to the LED D1 to provide a visual indication of the application of energy to the fastener 50. The engagement of switch SW2 opens the circuit and disconnects the LED from the energy source 194.

Figure 21:
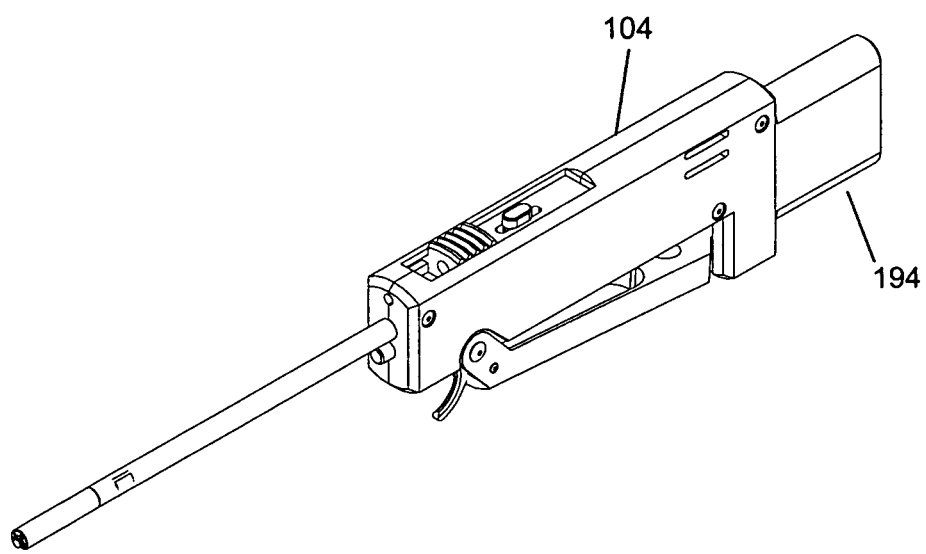
FIG. 21 depicts an isometric view of the medical device of FIG. 12 including an attached energy source.

The energy source 194 can be an external energy source connected to the handle 104 of the medical device 100. Alternatively, as shown in FIG. 21, the energy source 194 is a battery pack 194 connected to the handle 104 of the medical device 100. The battery 194 can include disposable batteries, or in the alternative, rechargeable batteries.

Figure 22:
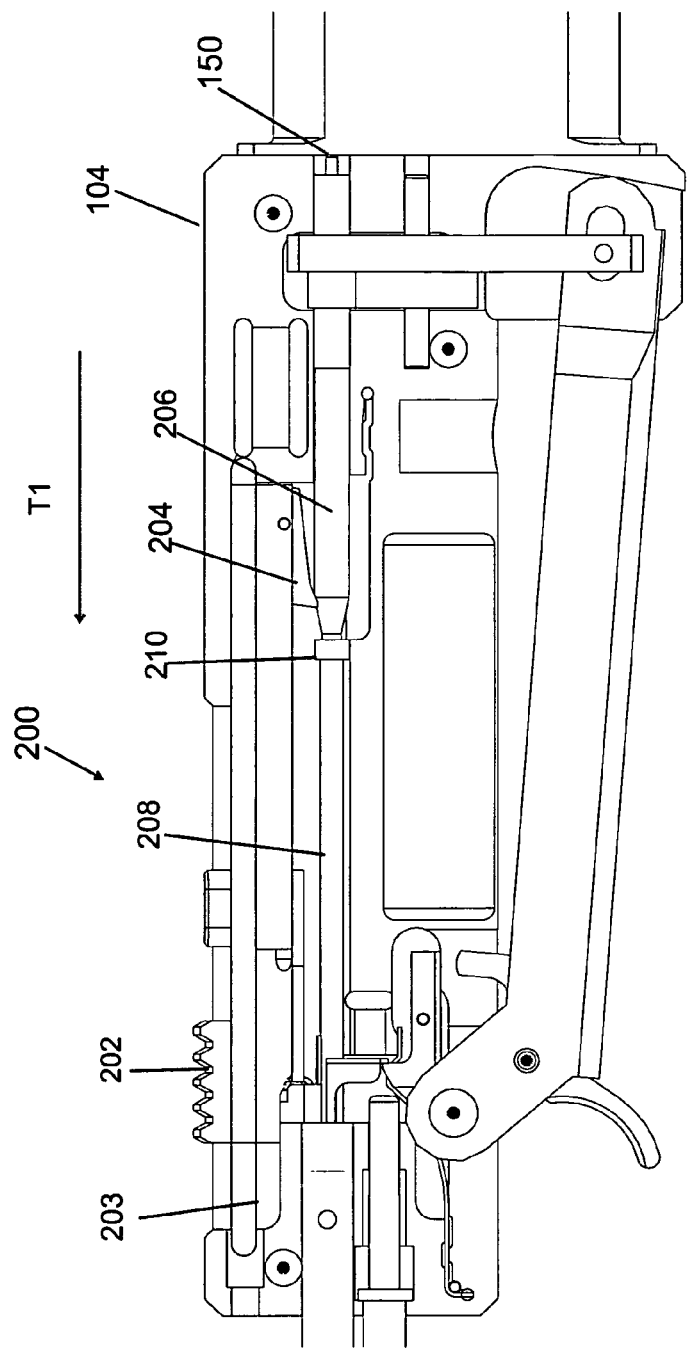
FIG. 22 depicts a sectional view of the medical device of FIG. 12 showing the handle portion of the ejector mechanism.
Figure 23:
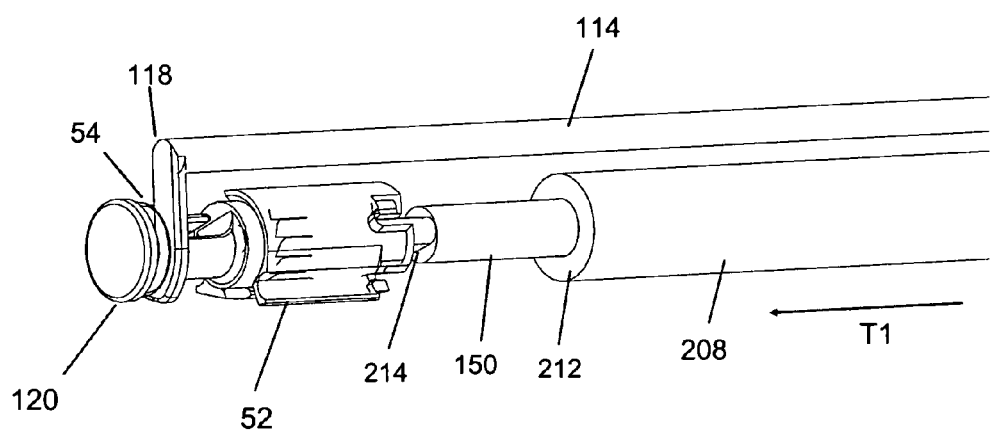
FIG. 23 depicts a sectional view of the medical device of FIG. 12 showing the tip portion of the ejector mechanism.

The ejection mechanism is used to eject the bonded fastener 50 from the tip 102 of the medical device 100. Referring to FIGS. 22 and 23, an ejection mechanism 200 includes an ejector 202 slidably mounted to the handle 104 of the medical device 100. The ejector 202 is maintained in a first position by an ejector biasing member 203. The ejector 202 includes an ejector pawl 204 for engaging a ratchet bushing 206, wherein the ratchet bushing 206 is slidably mounted about the center rod 150. The ejector 202 is slid, with respect to the handle 104, from the first position to a second position, such that the ejector pawl 204 engages and translates the ratchet bushing 206 along the center rod 150 in the first direction T1. The ratchet bushing 206 is positioned in abutting relations with a first end portion 210 of an ejector tube 208, wherein the ejector tube 208 is similarly slidingly mounted about the center rod 150, traversing the handle 104 and tubular member 103 to the tip 102. The ejector tube 208, and the center rod 150, is supported through the tubular member 103 by the first and second tube supports 113 and 115. The translation of the ratchet bushing 206 translates the ejector tube 208 in the first direction T1. The translation of the ejector tube 208 moves a second end portion 212 of the ejector tube 208 into an engagement with a trailing end portion 214 of the fastener 50, sliding the fastener 50 out of the tip portion 102 of the medical device 100.

Figure 24:
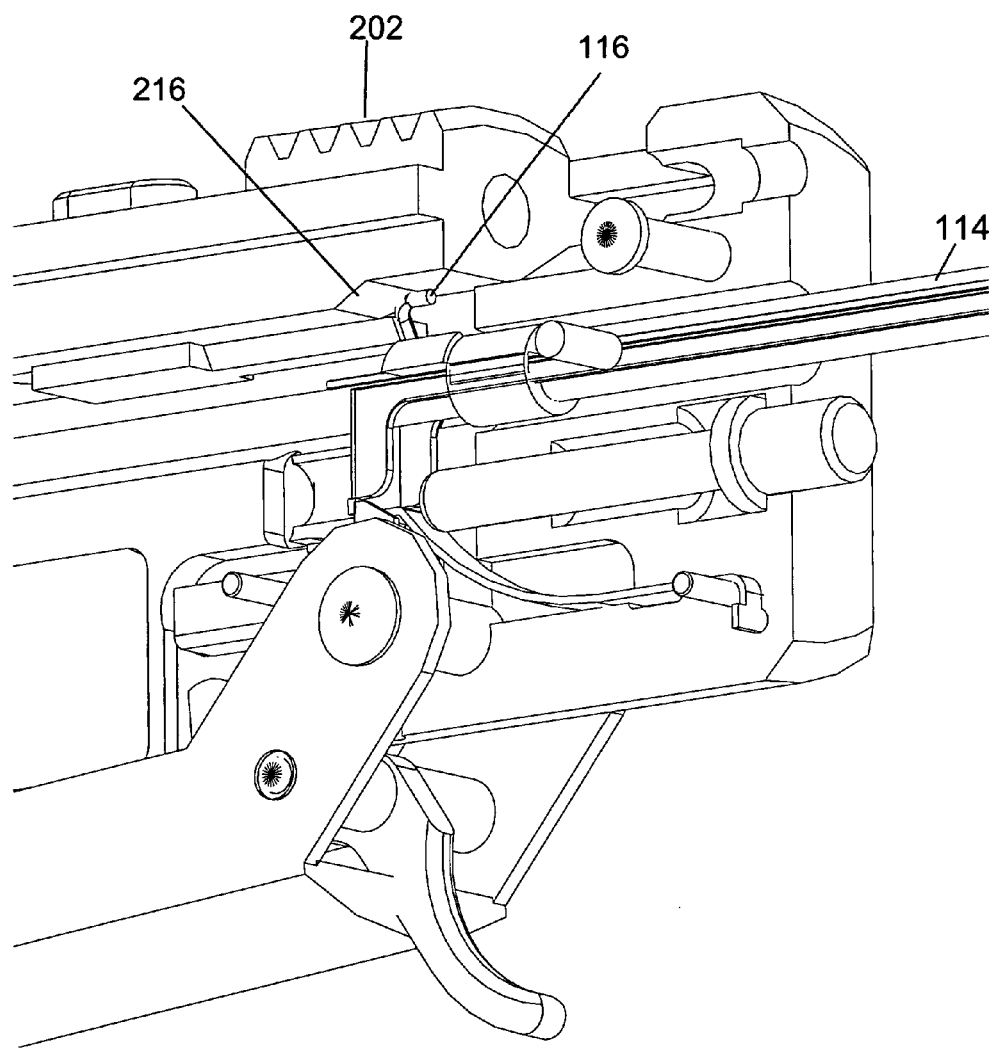
FIG. 24 depicts a front isometric sectional view of the medical device of FIG. 12 of the ejector mechanism of FIG. 22.

Referring now to FIG. 24, simultaneously as the ejector 202 is moved from the first position to the second position, an angular leading end portion 216 of the ejector 202 engages the first end portion 116 of the transfer rod 114. The angular configuration of leading end portion 216 of the ejector 202 results in a rotation of the transfer rod 114 as the ejector 202 is moved from the first position to second position. As the transfer rod 114 is rotated, the second end portion 118 of the transfer rod 114 releases the leading end portion 120 of the second fastener member 54. As such, the fastener 50 is ejected from the medical device 100.

Figure 25:
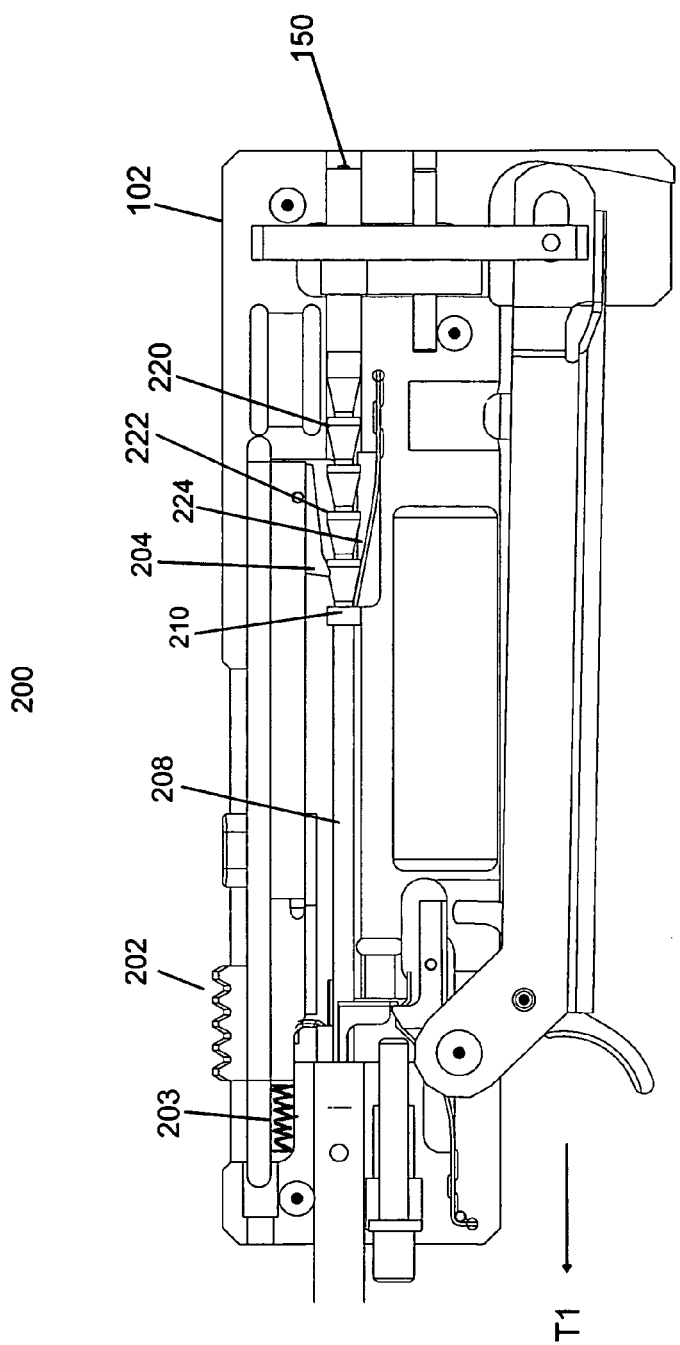
FIG. 25 depicts a sectional view of the medical device of FIG. 12 showing the handle portion of a multi-fastener ejector mechanism.

The above medical device 100 is disclosed as containing a single fastener 50 in the tip portion 102. However, it is contemplated the medical device 100 can include multiple fasteners 50. Referring to FIG. 25, the ejection mechanism 200 includes an ejector 202 slidably mounted to the handle portion 102 of the medical device 100. The ejector 202 is maintained in a first position by an ejector biasing member 203. The ejector 202 includes an ejector pawl 204 for engaging an ejector bushing 220, wherein the ejector bushing 220 is slidably mounted about the center rod 150. The ejector bushing 220 includes a plurality of ratchet members 222. The ejector 202 is slid, with respect to the handle 104, from the first position to the second position, such that the ejector pawl 204 engages a ratchet member 222, translating the ejector bushing 220 along the center rod 150 in the first direction T1. The ejector bushing 220 is prevented from translating along the center rod 150 in a direction opposite to the first direction T1 by the engagement of a locking member 224 with the at least one of the ratchet members 222 of the ejector bushing 220.

The ejector bushing 220 is positioned in an abutting relation with a first end portion 210 of an ejector tube 208, wherein the ejector tube 208 is similarly slidingly mounted about the center rod 150. The translation of the ejector bushing 220 translates the ejector tube 208 in the first direction T1.

Figure 26:
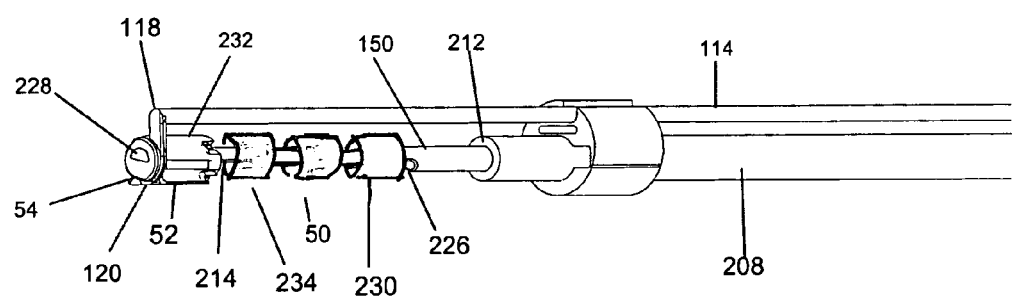
FIG. 26 depicts a sectional view of the medical device of FIG. 12 showing the tip portion of the multi-fastener ejector mechanism.
Figure 27:
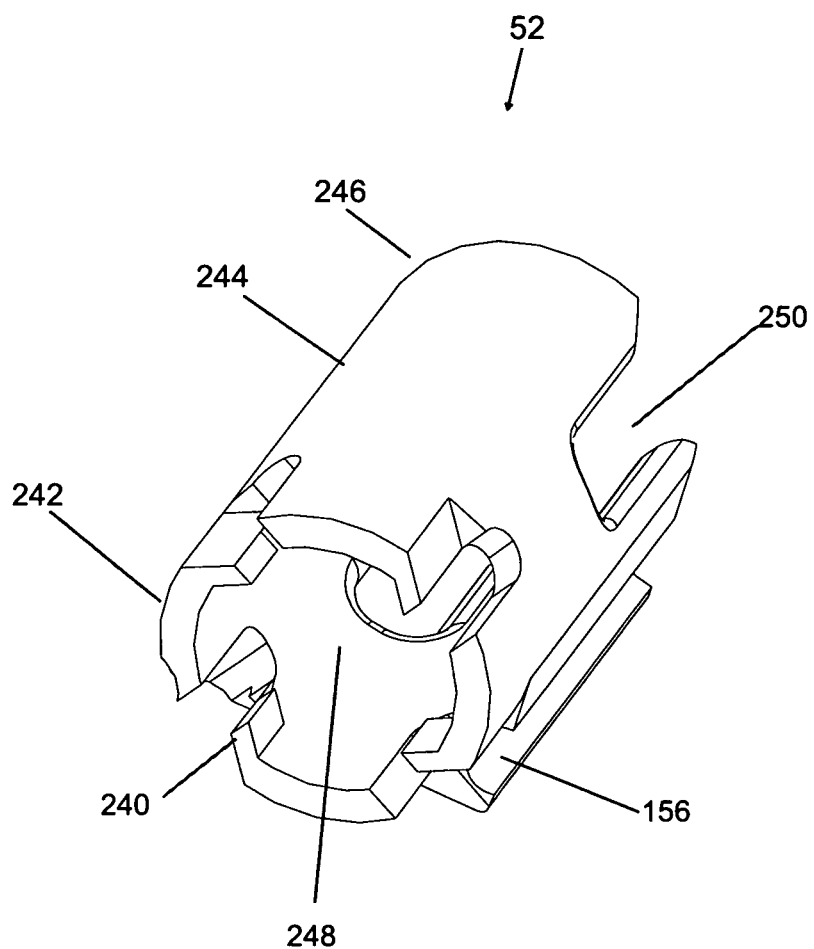
FIG. 27 depicts a first isometric view of a first member of a fastener for use with the ejector mechanisms of FIGS. 12 and 26.
Figure 28:
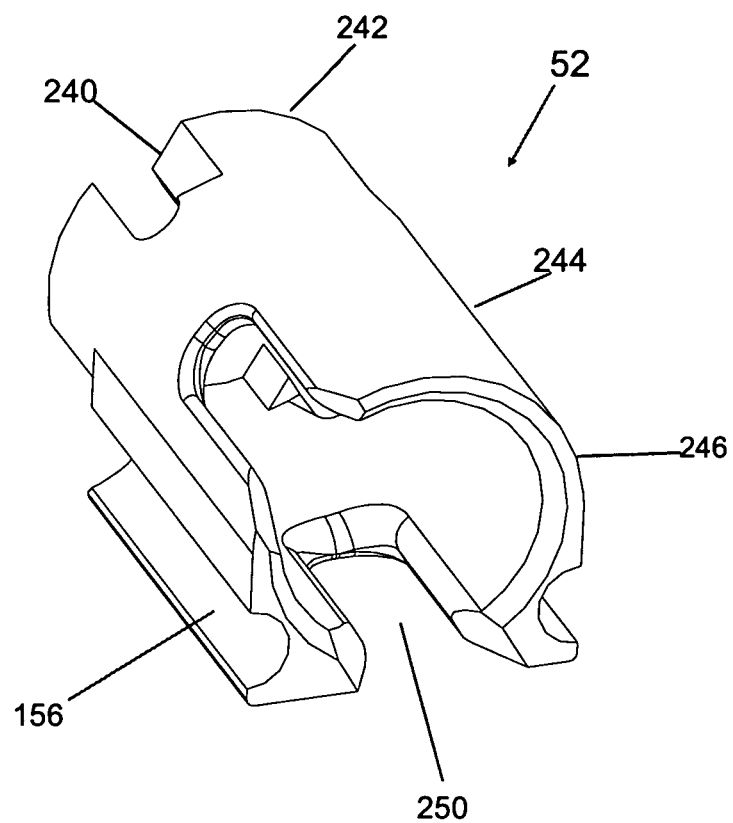
FIG. 28 depicts a second isometric view of a first member of a fastener for use with the multi-fastener ejector mechanism of FIGS. 12 and 26.
Figure 29:
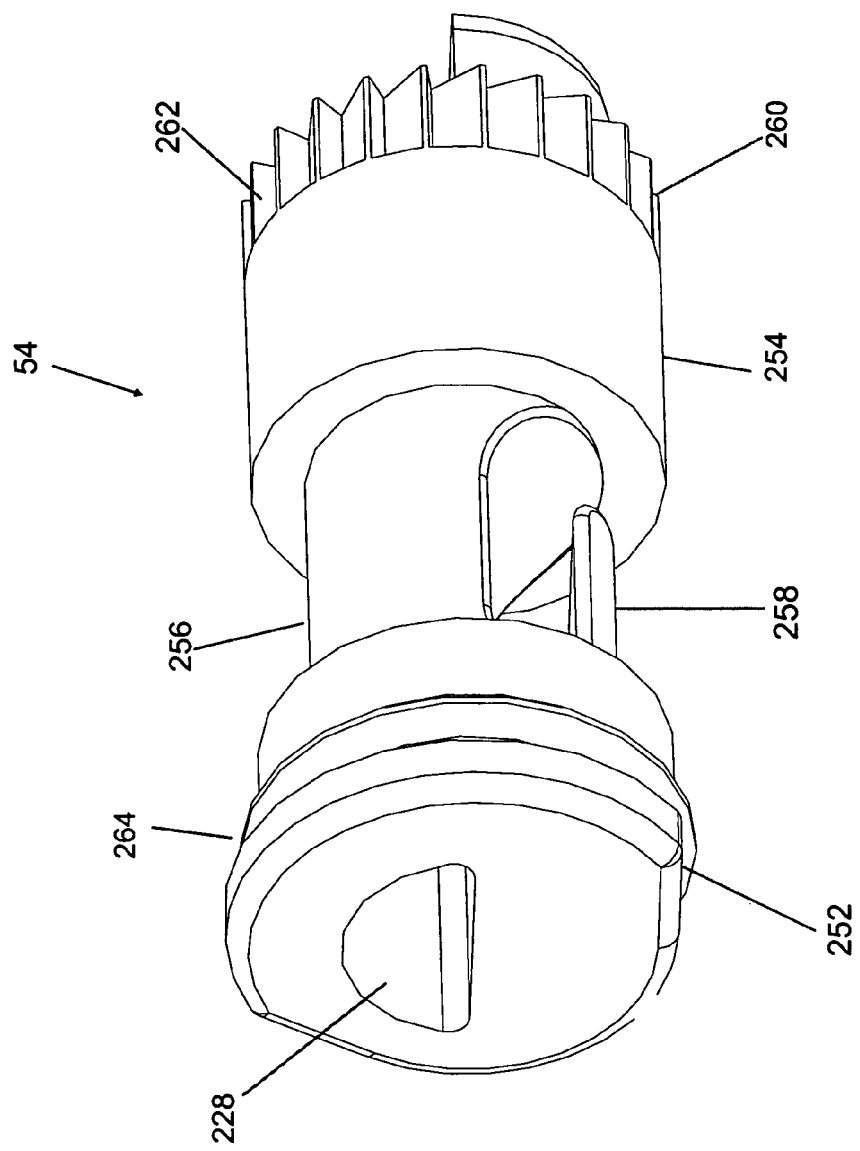
FIG. 29 depicts a first isometric view of a second member of a fastener for use with the first member of FIGS. 27 and 28.
Figure 30:
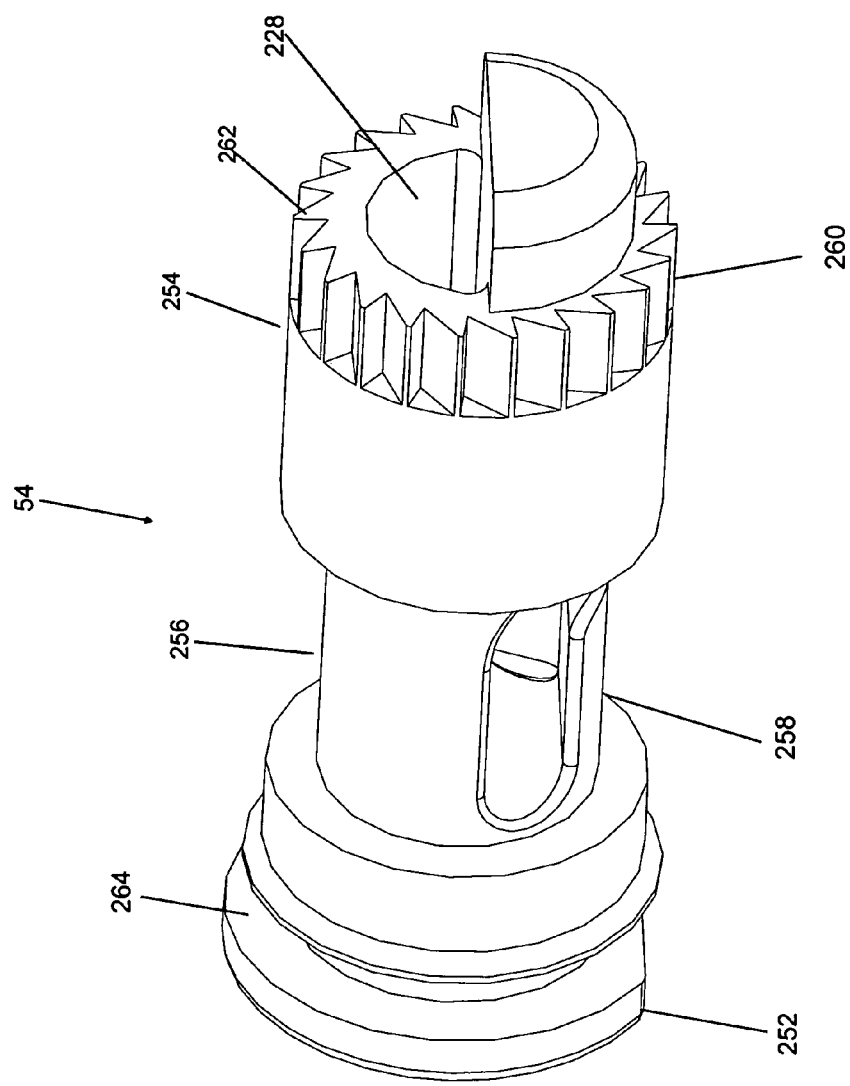
FIG. 30 depicts a second isometric view of a second member of a fastener for use with the first member of FIGS. 27 and 28.

Referring to FIG. 26, the tip 102 includes a plurality of fasteners 50 slidingly positioned onto an end portion 226 of the center rod 150. The end portion 226 of the center rod 150 is shaped to slidingly engage a passage 228 through the second fastener member 54, such that a plurality of fasteners 50 are serially positionable on the end portion 226 of the center rod 150.

The translation of the ejector tube 208 moves a second end portion 212 of the ejector tube 208 into an engagement with a first fastener 230, sliding the plurality of fasteners 50 along the end portion 226 of the center rod 150, such that a loaded fastener 232 is slid out of the tip 102 of the medical device 100. Upon ejection of the loaded fastener 232, the next adjacent fastener 234 is loaded into the tip 102 of the medical device 100.

Simultaneously, as shown in FIG. 24, as the ejector 202 is moved from the first position to the second position, an angular leading end portion 216 of the ejector 202 engages the first end portion 116 of the transfer rod 114. The angular configuration of leading end portion 216 of the ejector 202 resulted in a rotation of the transfer rod 114 as the ejector 202 is moved from the first position to second position. As the transfer rod 114 is rotated, the second end portion 118 of the transfer rod 114 releases the leading end portion 120 of the second fastener member 54 of the loaded fastener 232.

Upon ejection of the loaded fastener 232, the ejector 202 is moved from the second position to the first position. The angular configuration of leading end portion 216 of the ejector 202 results in a rotation of the transfer rod 114, such that the second end portion 118 of the transfer rod 114 engages the leading end portion 120 of the second member 54 of the next adjacent fastener 234 now loaded into the tip 102 of the medical device 100. The ejector mechanism 200 can be used to serially eject and load each fastener 50 onto the tip portion of the medical device 100.

In a method of use, the medical device 100 is used to secure a fastener 50 to a suture 74, thereby preventing relative movement of the suture 74 with respect to a body tissue. The fastener 50 may be supported in the tip 102 such that an actuation of a transfer mechanism 110 extends the second member 54 from the first member 52 to capture the suture 74. Upon capture, the ratcheting mechanism 103 draws the fastener 50 to the body tissue, applying a tension to the suture 74 and the body tissue to prevent relative movement between the suture 74 and the body tissue. The fixation mechanism 170 secures the fastener 50 to the suture with the application of an energy to the fastener 50, bonding the first and second fastener members 52 and 54 together. The ejector mechanism 200 ejects the bonded fastener 50 from the medical device 100. The medical device 100 can include a single fastener 50, or optionally, include multiple fasteners 50 serially loaded within the tip portion 102. The serially loaded fasteners 50 can be systematically bonded to individual sutures 74 to prevent a relative movement of the sutures 74 with respect to the body tissue.

Referring to FIGS. 27-30, there is provided and exemplary fastener 50 for uses with the devices of FIGS. 12-26. The first member 52 of the fastener 50 includes at least one key element 240 circumferentially positioned about an end portion 242 of the outer shell 244. The key element 240 may be formed from bending a portion of the end of the shell 244 inwards toward the center of the first member 52. Alternatively, one or more key elements 240 may be formed on the interior surface of the axial passage 248. More than one key 240 element may be provided as well. For instance, the interior surface of the axial passage 248 may have a plurality of inwardly projecting key elements 240 that are angled to allow gear teeth 262 on the second member 54 to slip over them in one direction, but not in the other. A pair of longitudinal channels 156 are positioned along the outer shell 244 to slidingly engage the tip 102 of the device.

The outer shell 244 of the first member includes a pair of suture slots 250 that extend from a central location of the shell 244 toward a second end portion 246. The suture slots 250 may be generally linear so that that they travel generally in a direction parallel to a central longitudinal axis. Alternatively, one or more slots 250 may curve around a portion of the shell 244 and form a curved or arced opening.

The second member 54 of the fastener 50 includes a first and second end portion 252 and 254 having a center portion 256 disposed there between. The center portion 256 includes a hook member 258 configured for capturing a suture. The cross sectional areas of the first and second end portions 252 and 254 are dimensioned such that the second member 54 is slideably and rotatably positionable through the axial passage 248 of the first member 52. The cross sectional area of the center portion 256 is less then the cross section areas of first and second end portions 252 and 254, providing spacing between the outer shell 244 of the first member 52 and the center portion 256 of the second member 54.

An integrated gear portion 260 having a one or more angled gear teeth 262 radially positioned about the second end portions 254. Upon insertion of the second member 54 into the axial passage 248 of the first member 52, the key element 240 engages the gear portion 260 of the second member 54. The angular positioning of the gear teeth 262, the key element 240, or both permits the second member 54 to be rotated in only one direction with respect to the first member 52.

The first end portion 252 of the second member includes a radial channel 264 there about. The radial channel 264 is configures such that the second end 118 of the transfer rod 114 engages the radial channel, where the swing arm 119 of the second end 118 of the transfer rod 114 is rotated into the radial channel 264.

The second end portion 254 includes a passage 228 therein, such that the second member 54 can be slideably positioned onto an end portion 226 of the center rod 150. The end portion 226 of the center rod 150 is shaped to slidingly engage a passage 228. The passage 228 can extend partially through the second member, such that only a single fastener 50 can be positioned on the end portion 226 of the center rod 150. Alternatively, the passage 228 can extend completely through the second member 54, such that a plurality of fasteners 50 are serially positionable on the end portion 226 of the center rod 150.

Figure 31:
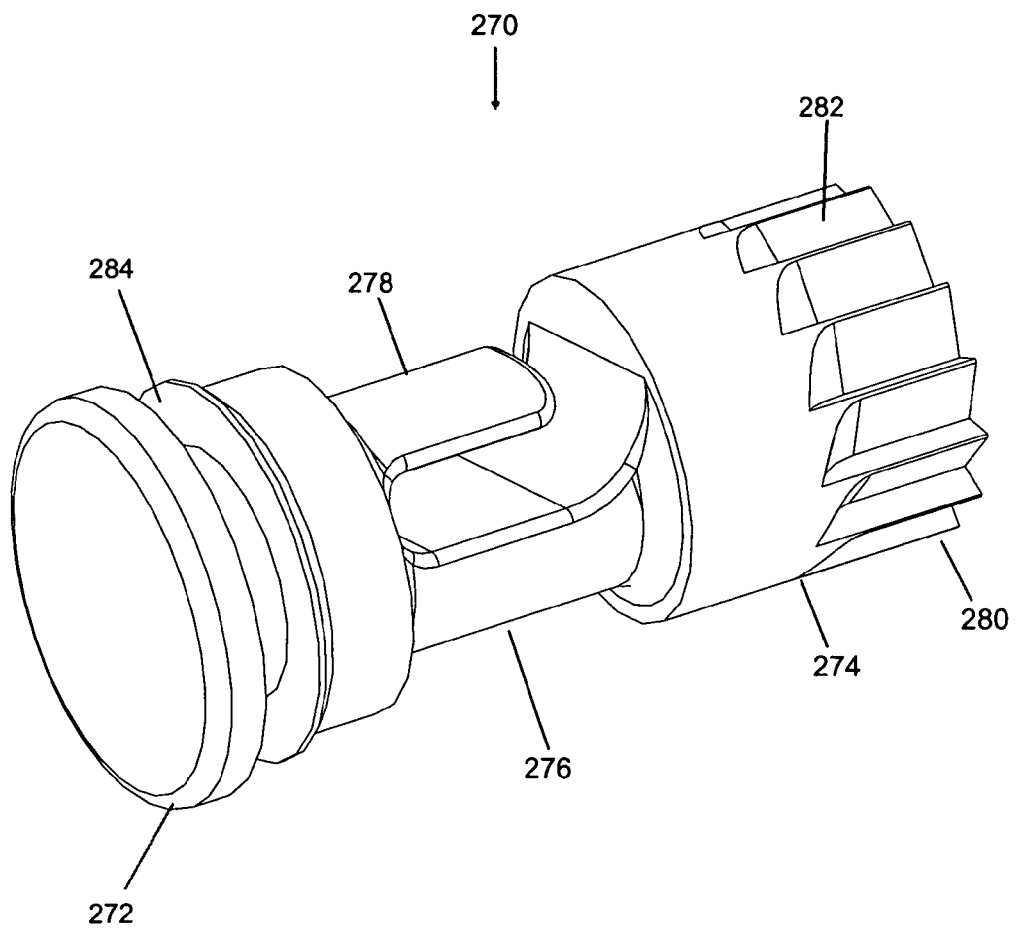
FIG. 31 depicts a first isometric view of an alternative second member of a fastener.
Figure 32:
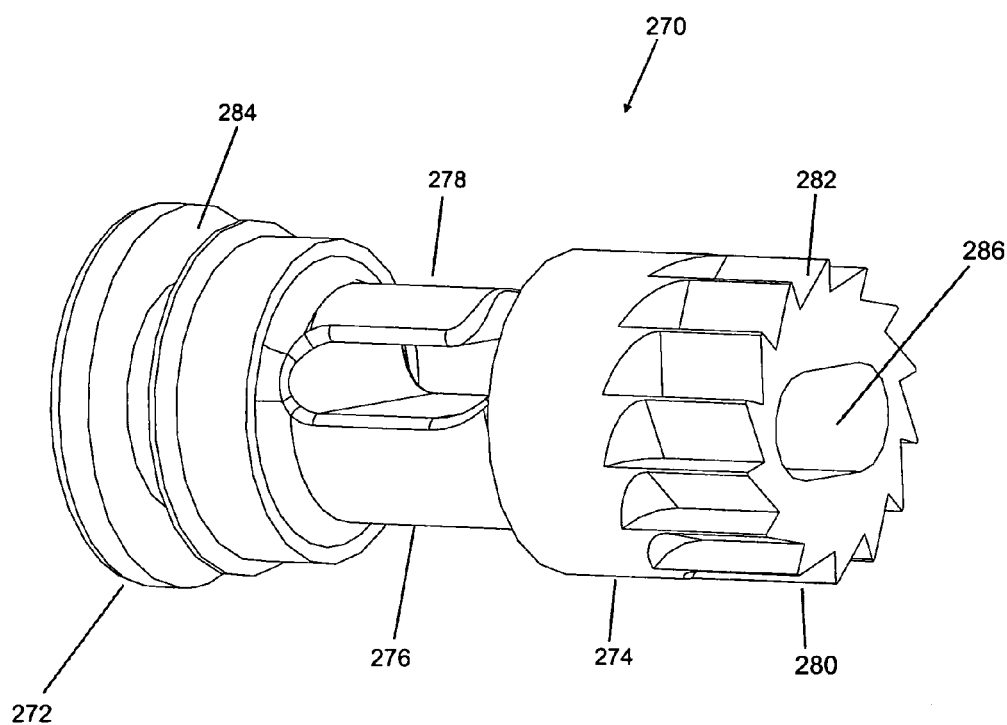
FIG. 32 depicts a second isometric view of the alternative second member of a fastener.

Referring to FIGS. 31 and 32 an alternative second member 270 of the fastener 50 includes a first and second end portion 272 and 274 having a center portion 276 disposed there between. The center portion 276 includes a hook member 278 configured for capturing a suture. The cross sectional areas of the first and second end portions 272 and 274 are dimensioned such that the second member 270 is slideably and rotatably positionable through the axial passage 248 of the first member 52. The cross sectional area of the center portion 276 is less than the cross section areas of first and second end portions 272 and 274, providing spacing between the outer shell 244 of the first member 52 and the center portion 276 of the second member 270.

An integrated gear portion 280 having a one or more angled gear teeth 282 radially positioned about the second end portions 274. Upon insertion of the second member 70 into the axial passage 248 of the first member 52, the key element 240 engages the gear portion 280 of the second member 270. The angular positioning of the gear teeth 282, the key element 240, or both permits the second member 270 to be rotated in only one direction with respect to the first member 52.

The first end portion 272 of the second member includes a radial channel 284 there about. The radial channel 284 is configure such that the second end 118 of the transfer rod 114 engages the radial channel, where the swing arm 119 of the second end 118 of the transfer rod 114 is rotated into the radial channel 284.

The second end portion 274 includes a passage 286 therein, such that the second member 74 can be slideably positioned onto an end portion 226 of the center rod 150. The passage 286 is aligned along the central longitudinal axis of the second member 270. The end portion 226 of the center rod 150 is shaped to slidingly engage a passage 286. The passage 286 can extend partially through the second member, such that only a single fastener 50 can be positioned on the end portion 226 of the center rod 150.

It is contemplated that the fasteners of the present invention may be formed of many different materials. The fasteners of the present invention may be made of, but are not limited to, a degradable, biodegradable, bioerodible, or bioabsorbable materials.

Alternatively, the fasteners may be formed of a material which is not degradable, biodegradable, bioerodible, or bioabsorbable. For example, the fastener may be formed of poly ether-ether-keton (PEEK), such as "PEEK-OPTIMA" (trademark). Alternatively, the fasteners may be formed of a para-dimethylamino-benzenediazo sodium sulfonate, such as "Dexon" (trademark). If desired, the fastener may be formed of nylon. Additionally, the fastener may be made of a heat shrink material.

Furthermore, the fasteners may include metallic material, polymeric material, ceramic material, composite material, body tissue, synthetic tissue, hydrophilic material, expandable material, compressible material, heat bondable material, and combinations thereof. Examples of body tissue include bone, collagen, cartilage, ligaments, or tissue graft material like xenograft, allograft, and autograft. The fastener may also be made from a porous matrix or mesh of biocompatible and bioresorbable fibers acting as a scaffold to regenerate tissue.

Moreover, the fasteners disclosed herein may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immuno suppressants, fibrin, osteoinductive materials, apatite compositions, germicides, viable cells, fetal cells, stem cells, enzymes, proteins, hormones, cell therapy substances, gene therapy substances, and combinations thereof. These therapeutic substances may be combined with the materials used to make the fasteners to produce a composite fastener. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

It is contemplated that the viable cells may be incorporated or positioned on the fastener of the present invention. The viable cells may be any desired type of viable cells. It is contemplated that the viable cells may correspond to cells which were in a damaged organ or other portion of a patient's body. More than one type of viable cell may be positioned on the fastener.

When the fastener is to be positioned in an organ, it is contemplated that the viable cells on the fastener will have characteristics associated with the characteristics of normal cells in the organ in which the support structure is to be positioned. Many organs contain cells which have different characteristics and perform different functions within the organ. It is contemplated that the viable cells on the fastener may have different characteristics corresponding to the different characteristics of cells of an organ. When the fastener is to be positioned outside of an organ, the cells positioned on the support structure may have any desired characteristic or combination of characteristics.

It is also contemplated that the viable cells can be pluripotent cells that are directed to differentiate into the desired cell type or types. One example of such cells is stem cells. The differentiation can be controlled by applying or exposing the cells to certain environmental conditions such as mechanical forces (static or dynamic), chemical stimuli (e.g. pH), and/or electromagnetic stimuli.

More than one type of cell may be positioned on the fastener. The type of cell positioned at a particular location on the fastener will be determined by the orientation of the support structure in a patient's body and by the specific type of tissue desired at a particular location in a patient's body. For example, stromal cells may be positioned at a location where foundation tissue is desired and another type of cell may be positioned at locations where it is desired to have tissue perform a special function.

In order to promote the attachment of the viable cells to the fastener, the fastener can be pretreated with an agent that promotes cell adhesion. One such agent is an organic substance based on a biofilm. A biofilm is a slimy, glue-like substance that forms when bacteria attach to surfaces exposed to water. Typically, colonies of biofilm bacteria are unwanted as they carry out a variety of detrimental reactions. However, a sterile biofilm may be used to promote initial attachment of cells to the fastener.

The sterile biofilm could be engineered to isolate the glue-like substance while eliminating the adverse properties of the bacteria. The resulting sterile glue-like substance would be used to help the cells stick to the fastener. The engineered biofilm could be added to the fastener in the laboratory that produces the fastener or just prior to the addition of the cells by the user. Alternatively, the biofilm and fastener could be combined intra-corporally.

This biofilm also could be used as an independent polysaccharide based adhesive with mild to moderate adhesion forces. The biofilm could serve as a surgical adhesion or grouting for cells, for tissue fixation (soft tissue to soft tissue, soft tissue to bone, etc.) and as a sealant.

Additionally, it is contemplated that pharmaceutical agents such as tissue inductive growth factors, additives, and/or other therapeutic agents may be provided on or incorporated into the suture fastener or retainer of the present invention. Such additives may include materials such as plasticizers, citrate esters, hexametholsebacate, antibiotics (e.g., tetracyclines, penicillins, mefronidazole, clindamycin, etc.), to prevent infection, etc., or to accomplish other desired conditions or results, including for example, tissue inductive growth factors to promote a growth of tissue. Additional additives or therapeutic agents include osteoinductive, biocidal, or anti-infection substances. Suitable osteoinductive substances include, for example, growth factors. The growth factors may be selected from the group of IGF (insulin-like growth factors), TGF (transforming growth factors), FGB (fibroblast growth factors), EGF (epidermal growth factors), BMP (bone morphogenic proteins), and PDGF (platelet-derived growth factors).

The inductive growth factors, additives, and/or other therapeutic agents may be provided on or incorporated into the fastener prior to connection to the suture. Alternatively, the inductive growth factors, additives, and/or other therapeutic agents may be provided on or incorporated after connection to the suture.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The suture of the present invention may be made of metallic material, non-metallic material, composite material, polymeric material, co polymeric material, or combinations thereof. The members may be degradable, biodegradable, bioabsorbable, or nonbiodegradable. For example, suture materials that can be used include, but are not limited to, polyethylene, polyester, cat gut, silk, nylon, polypropylene, linen, cotton, and copolymers of glycolic and lactic acid. They suture materials may be threadlike, monofilament, multifilament, braided, or interlaced.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel.

An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled, Apparatus and Method for Use in Positioning a Suture Anchor, discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

Moreover, the devices and methods of the present invention may by used to approximate a skin incision where there may be undue tension on the skin. Fasteners may be placed on opposite sides of the incision, and a suture or cable may be placed between the fasteners. When the suture is tensioned, the skin may be pulled together and held until the skin tissue relaxes. Then, the fasteners may be unlocked, and the suture may be tensioned again to further approximate the skin incision. The locking and unlocking of the fasteners along with the tensioning of the suture may be repeated until the incision is fully closed.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

In addition, intramedullary fracture fixation and comminuted fracture fixation may be achieved with the devices and methods of the present invention. For example, a plate or rod may be positioned within or against the fractured bone. A fastener may be driven across the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled, Surgical Devices Assembled Using Heat Bondable Materials. For example, the fasteners of the present invention may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the fasteners and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the fasteners and methods described and incorporated herein may be used to approximate the damaged portion of the vessel.

Although the invention has been described primarily on a macroscopic level, it is also envisioned that the present invention can be used for microscopic applications. For example, in the repair of nerve tissue, individual cells or fibers may need to be repaired. Similarly, muscle repair may require tightening of individual muscle fibers.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is embodied by the following claims.

What is claimed is:

1. A suture management device comprising:
   a first member including a curved outer surface, the first member having a longitudinal passage with a longitudinal axis, an open end, a first engagement feature positioned about the longitudinal passage, a first suture aperture, and a second suture aperture; and
   a second member configured for insertion into the open end of the longitudinal passage of the first member, the second member having a second engagement feature configured to engage the first engagement feature, the second member having a suture passage extending through the second member, the suture passage configured to align with the first and second suture apertures to enable suture to pass through the suture passage and the first and second suture apertures,
   wherein the first and second members are configured to wrap a portion of suture around a portion of the second member between the first and second members,
   wherein at least one of the first and second engagement features is configured to allow rotation of said second member relative to said first member in a first direction but resist rotation in a second direction,
   wherein the suture management device is configured for insertion through tissue.

2. The suture management device of claim 1, wherein an end of the second member further comprises an instrument recess for engagement by a medical device.

3. The suture management device of claim 1, wherein an end of the second member includes a radial channel for engagement by the medical device.

4. The suture management device of claim 1, wherein the first member includes a channel for engagement by the medical device to restrict rotation of the first member.

5. The suture management device of claim 1, wherein the suture management device is configured for insertion into a bone.

6. The suture management device of claim 5, wherein the heat utilized to bond the first and second members is generated by an energy selected from the group consisting of radio frequency energy, laser energy, microwave energy, ultrasound energy, resistive heat energy, contact heating energy, and combinations thereof.

7. The suture management device of claim 1, wherein the first member includes an end opposite the open end,
   wherein the first and second suture apertures are formed through the first member at a location disposed between the open end and the end opposite the open end; and
   when inserted into the longitudinal passage, the first member and the second member are sized relative to each other, proximate the first and second suture apertures in the first member, to form a gap between the first member and the second member, into which suture is configured to be wound.

8. The suture management device of claim 1, wherein the first and second suture apertures are formed through the first member at a location disposed between the open end and an end opposite the open end; and
   when inserted into the longitudinal passage, the second member has a smaller cross sectional area adjacent the first and second suture apertures than a cross sectional area of a first end and a second end of the second member.

9. The suture management device of claim 1, wherein at least the first or second member includes PEEK.

10. The suture management device of claim 1, wherein the first and second engagement features are configured to incrementally tension suture.

11. The suture management device of claim 1, wherein at least the first member is expandable.

12. The suture management device of claim 1, wherein the suture management device is configured for utilization in fixation of soft tissue to bone.

* * * * *